(12) United States Patent
Aberg

(10) Patent No.: US 7,718,674 B2
(45) Date of Patent: May 18, 2010

(54) METHODS OF RELIEVING NEUROPATHIC PAIN WITH THE S-ISOMER OF 2-{2[N-(2-INDANYL)-N-PHENYLAMINO] ETHYL}PIPERIDINE

(75) Inventor: Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 983 days.

(21) Appl. No.: 11/236,263

(22) Filed: Sep. 27, 2005

(65) Prior Publication Data

US 2006/0079559 A1   Apr. 13, 2006

Related U.S. Application Data

(60) Provisional application No. 60/613,386, filed on Sep. 27, 2004.

(51) Int. Cl.
A61K 31/445 (2006.01)
C07D 211/26 (2006.01)

(52) U.S. Cl. .................. 514/319; 514/318; 546/194; 546/205

(58) Field of Classification Search .............. 514/318, 514/319; 546/194, 205
See application file for complete search history.

(56) References Cited

U.S. PATENT DOCUMENTS

| | | | |
|---|---|---|---|
| 3,923,813 A | 12/1975 | Vanhoff et al. | |
| 3,923,815 A | 12/1975 | Vanhoff et al. | |
| 3,923,887 A | 12/1975 | Vanhoff et al. | |
| 3,943,172 A | 3/1976 | Vanhoof et al. | 260/570.5 P |
| 4,822,597 A | 4/1989 | Faust et al. | |
| 4,942,175 A | 7/1990 | Frawley, III | |
| 5,000,950 A | 3/1991 | Wuendisch | |
| 5,227,165 A | 7/1993 | Domb et al. | |
| 5,234,957 A | 8/1993 | Mantelle | |
| 5,368,860 A | 11/1994 | Sunami et al. | |
| 5,446,070 A | 8/1995 | Mantelle | |
| 5,589,192 A | 12/1996 | Okabe et al. | |
| 5,667,799 A | 9/1997 | Caldwell et al. | |
| 5,776,952 A | 7/1998 | Liedtke | |
| 5,840,755 A | 11/1998 | Liedtke | |
| 5,863,941 A | 1/1999 | Liedtke | |
| 5,914,118 A | 6/1999 | Yamamura et al. | |
| 5,958,443 A | 9/1999 | Viegas et al. | |
| 5,968,536 A | 10/1999 | Godfrey | |
| 6,004,566 A | 12/1999 | Friedman et al. | |
| 6,031,007 A | 2/2000 | Brodin et al. | |
| 6,060,085 A | 5/2000 | Osborne | |
| 6,075,059 A | 6/2000 | Reader | |
| 6,103,771 A | 8/2000 | Galer et al. | |
| 6,113,921 A | 9/2000 | Friedman et al. | |
| 6,299,902 B1 | 10/2001 | Jun et al. | |
| 6,383,511 B1 | 5/2002 | Cassel | |
| 6,387,392 B1 | 5/2002 | Saito et al. | |
| 6,413,987 B1 * | 7/2002 | Aberg et al. | 514/319 |
| 6,455,544 B1 | 9/2002 | Friedhoff et al. | |
| 6,458,807 B1 | 10/2002 | Pratt | |
| 6,482,838 B2 | 11/2002 | Pratt | |
| 6,528,086 B2 | 3/2003 | Zhang | |
| 6,576,646 B1 | 6/2003 | Pratt | |
| 6,620,435 B1 | 9/2003 | Osborne | |
| 6,645,521 B2 | 11/2003 | Cassel | |
| 6,673,363 B2 | 1/2004 | Luo et al. | |
| 6,689,795 B2 | 2/2004 | Pratt | |
| 2001/0041166 A1 | 11/2001 | Saito et al. | |
| 2002/0022052 A1 | 2/2002 | Dransfield | |
| 2003/0027833 A1 | 2/2003 | Cleary et al. | |
| 2003/0082225 A1 | 5/2003 | Mason | |
| 2003/0091619 A1 | 5/2003 | Spencer | |
| 2003/0124174 A1 | 7/2003 | Galer | |
| 2003/0138503 A1 | 7/2003 | Staniforth et al. | |
| 2003/0138505 A1 | 7/2003 | Fischer et al. | |
| 2003/0175328 A1 | 9/2003 | Shefer et al. | |
| 2004/0081681 A1 | 4/2004 | Vromen | |

FOREIGN PATENT DOCUMENTS

| | | |
|---|---|---|
| CA | 992547 | 7/1976 |
| CA | 997765 | 9/1976 |
| CA | 997786 | 9/1976 |
| CA | 1068289 | 12/1979 |
| EP | 0321870 | 11/1992 |
| EP | 0742207 | 8/2001 |
| EP | 1216685 | 6/2002 |
| GB | 1321424 | 6/1973 |
| GB | 1 405 444 | 9/1975 |
| GB | 1 468 347 | 3/1977 |
| WO | 9107169 | 5/1991 |
| WO | 9609829 | 4/1996 |
| WO | 9633706 | 10/1996 |

(Continued)

OTHER PUBLICATIONS

Lidocaine RN 137-58-6 (1984).*

(Continued)

*Primary Examiner*—Celia Chang
(74) *Attorney, Agent, or Firm*—Nields, Lemack & Frame, LLC

(57) ABSTRACT

The present invention relates to the S-isomers of anesthetic compounds, the methods of treatment therewith, the compounds being useful for inducing local anesthesia, analgesia and sleep.

16 Claims, 1 Drawing Sheet

FOREIGN PATENT DOCUMENTS

| | | |
|---|---|---|
| WO | 9817263 | 4/1998 |
| WO | 0076510 | 12/2000 |
| WO | 0185139 | 11/2001 |
| WO | 04000358 | 12/2003 |
| WO | 2004047819 | 6/2004 |

OTHER PUBLICATIONS

Anesthesia definition from answers.com. (2009) p. 1 from internet.*

*Vasoinhibitory Effects of NC 1005 and NC 1006, New Synthesized Antiarythmic Agents, In Isolated Rat Aorta*, N.Stake, et al., Gen. Pharmac. vol. 25, No. 6, pp. 1149-1156.

*Local Anesthetic Activity and Toxicity of Several Esters of p-Tertiary-Butylbenzoic Acid*, Lamar B. Dale, et al., Journal of the American Pharmaceutical Association, vol. XLII, No. 11, pp. 685-687.

Acta Pharmacol et toxicol, 1972, 31 p. 273-286; G.Aberg; "Toxicological and Local Anaesthetic Effects of Optically Active Isomers of Two Local Aneasthetic Compounds".

Dale et al.; "Local anesthetic activity and toxicity of several esters of p-tert-butylbenzoic acid" CA 48:8416 (1953).

J.Org. Chem. 1996, 61, 3849-3861; Ahmed F. Abdel-Magid et al.; "Reductive Amination of Aldehydes and Ketones with Sodium Triacetoxyborohydride. Studies on Direct and Indirect Reductive Amination Procedures".

Vanhoof et al., caplus AN 1974: 403674.

International Search Report dated Jul. 25, 2008.

T.W. Graham Solomons and C.B. Fryle Organic Chemistry, $9^{th}$ Edition, John wiley and Sons, Inc. pp. 183-184.

Office Actions from related U.S. Appl. No. 11/880,270 dated Oct. 10, 2008 and Jul. 8, 2008.

Office Actions from related U.S. Appl. No. 11/235,869 dated Nov. 5, 2008 and Jun. 4, 2008.

* cited by examiner

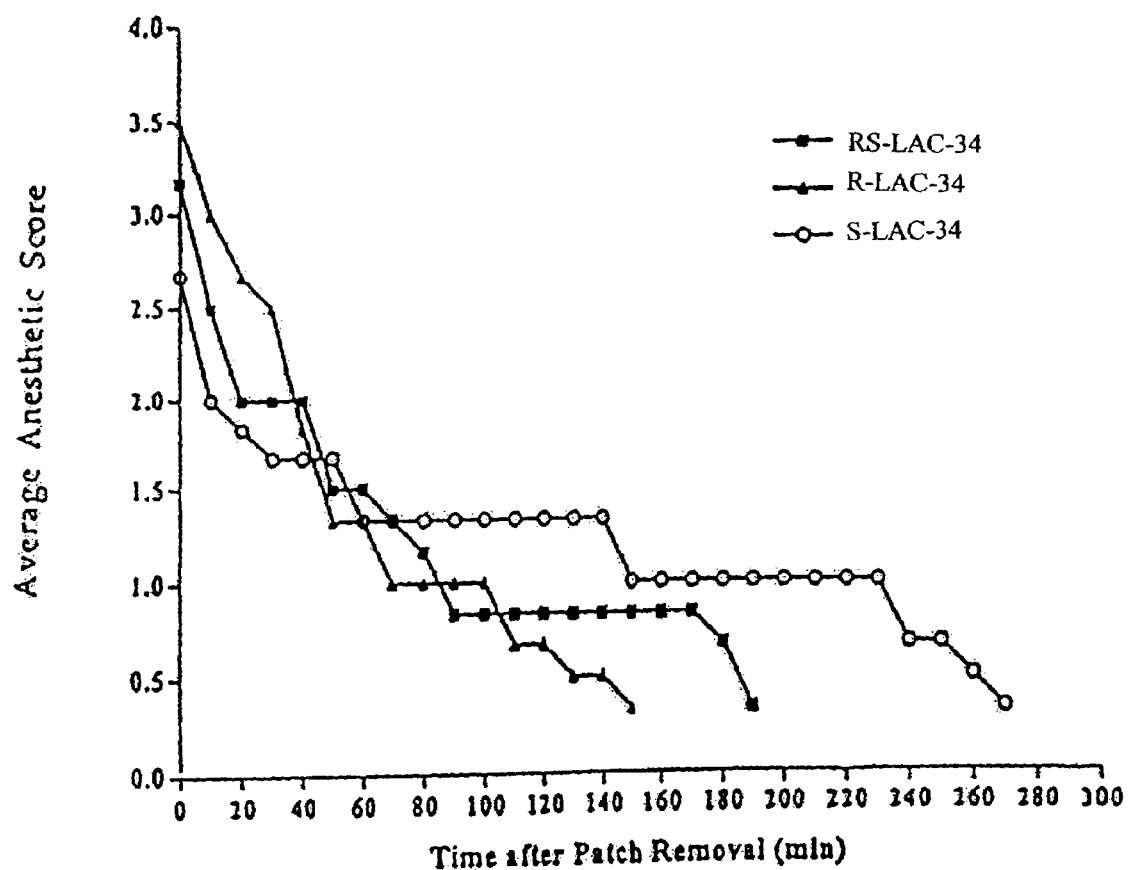

METHODS OF RELIEVING NEUROPATHIC PAIN WITH THE S-ISOMER OF 2-{2[N-(2-INDANYL)-N-PHENYLAMINO]ETHYL}PIPERIDINE

This application claims benefit to U.S. Provisional Patent Application Ser. No. 60/613,386, filed Sep. 27, 2004, the disclosure of which is hereby incorporated by reference.

FIELD OF THE INVENTION

The present invention relates to new nerve membrane stabilizing compounds and to methods of inducing local, topical or dermal anesthesia, by administering a composition containing at least one such chemical entity that has such penetration properties that it in a short period of time can reach the site of action on the nerve ending or a nerve in a concentration that will block the initiation or conduction of nerve impulses for a long period of time. The invention also relates to compositions containing at least one of the compounds of the present invention that are particularly useful for ocular and dermal anesthesia and for other forms of local anesthesia, such as for example infiltration anesthesia and nerve blocks.

The chemical compounds of this invention also have pharmacological properties that render the compounds useful in preventing and treating pain. The compounds of the present invention are useful for the prevention of pain in connection with certain medical procedures such as the insertion of an injection needle, surgical procedures and for the treatment of pain such as in connection with the above mentioned medical procedures, insect bites, sunburn, neuropathic pain and for the treatment of shingles and urogenital pain, including hemorrhoids.

Induction of anesthesia and prevention and treatment of pain using the compounds of this invention may be achieved by applying compositions containing the chemical entities on the skin or by applying compositions containing the chemical entities on mucosal membranes or by injecting solutions of the chemical entities to infiltrate biological tissues with the solutions or by injecting solutions of the chemical entities in the anatomical vicinity of nerves, thereby allowing the chemical entities to penetrate the biological tissues and cause dermal anesthesia, topical anesthesia, infiltration anesthesia and/or nerve blocks. Ocular, nasal, rectal, urogenital and other parenteral routes of administration are also contemplated.

Thus, the present invention provides effective methods for treating humans and animals with topical, dermal and local anesthetic compositions, while reducing undesirable side effects, for example local burning and itching and particularly tissue toxicity resulting in necrosis.

The compounds may also be used to treat conditions, comprising convulsions, hiccup and cardiac arrhythmias and can be used to inhibit sodium and potassium ion fluxes over cell membranes in the body.

The present invention relates to optically active S-isomers of a compound having the formula:

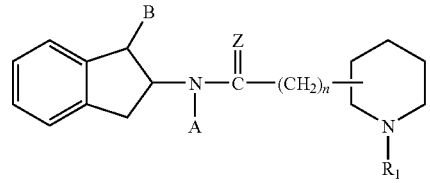

Formula I or a pharmaceutically acceptable salt, base, or mixture thereof, wherein n is equal to 0, 1, 2, or 3, Z represents two hydrogen atoms or an oxygen atom, the $(CH_2)_n$ group having a straight or branched chain, B represents hydrogen, an alkoxy radical containing 1 to 3 carbon atoms or a group of the formula

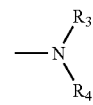

in which $R_3$ and $R_4$ may independently be selected from the group consisting of methoxy, ethoxy, a lower alkyl or hydroxyalkyl radical containing 1 to 3 carbon atoms, whereby $R_3$ may also represent hydrogen, A is a 2-pyridyl radical, an unsubstituted phenyl radical or a phenyl radical substituted by at least one substituent in the ortho, meta and/or para position, and $R_1$ represents a hydrogen, or a lower alkyl or hydroxyalkyl containing 1 to 4 carbon atoms and the piperidine nucleus is attached at the 2-, 3-, or 4-position.

The present invention also relates to a compound named S-2-{2-[N-(2-indanyl)-N-phenylamino]ethyl}piperidine, hereinafter called S-LAC-34 and to the processes for preparing S-LAC-34 and the salts thereof, to methods for using S-LAC-34 as a local anesthetic agent, to methods for using S-LAC-34 as an analgesic agent, and to pharmaceutical formulations containing S-LAC-34.

The invention also refers to compositions, containing at least one of the chemical entities and combinations of the present chemical entities with various other chemical entities and with various penetration promoting devices.

BACKGROUND OF THE INVENTION

Local anesthetics are membrane stabilizing agents that block nerve conduction by decreasing or preventing permeability of the cell membrane to sodium ions produced during depolarization of the membrane. When administered to specific nerve pathways, effects such as analgesia (loss of pain sensation) and paralysis (loss of muscle power) can be achieved. Amide-type anesthetics, such as lidocaine, prilocaine, mepivacaine and bupivacaine, contain an "amide linker" and have been shown to possess local anesthetic effects and are widely used for infiltration anesthesia and for inducing nerve blocks. These compounds have limited use as dermal anesthetics since they have to be given in high concentrations, which increase the risk of tissue irritation and tissue damage. Other compounds, such as tetracaine and procaine, are better suited for dermal anesthesia since they may better penetrate through tissue. However, tetracaine and procaine contain an "ester linker" and are known to cause tissue irritation and to be unstable in-the human body where practically all tissues contain esterases.

Aberg, et al. developed a set of compounds known as "aminoindane piperidine compounds" for use as dermal and topical anesthetics that showed less tissue toxicity than ester-type local anesthetics. These aminoindane piperidine compounds, described in U.S. Pat. No. 6,413,987, the disclosure of which is hereby incorporated by reference, contain an amine linker group attached to the piperidine ring at the para, meta or ortho position. These compounds are described as potent membrane stabilizing agents with a prolonged anesthetic effect having a short onset of action and readily penetratable into various tissues, e.g., ocular tissue, mucosal tissue, rectal tissue and skin. One particular compound that has been identified as particularly useful for dermal anesthesia and as producing little, if any, tissue toxicity is 2-{2-[N-(2-indanyl)-N-phenylamino]ethyl}piperidine [RS-LAC-34, racemic mixture].

In addition to the aminoindane piperidine compounds described in U.S. Pat. No. 6,413,987, additional aminoindane compounds are described in a number of patents to Vanhoof, et al. (GB 1 321 424; U.S. Pat. No. 3,923,813; U.S. Pat. No. 3,923,815; and U.S. Pat. No. 3,923,887). These aminoindanes, having an N-substituted piperidine ring, are described as antiarrhythmic compounds that also possess local anesthetic activity.

Toxicity studies comparing aminoindanes described by Vanhoof et al. and the aminoindanes described by Aberg, et al. show that the N-substituted piperidine compounds of Vanhoof have no clinical usefulness as local or dermal anesthetics as these tertiary amines were found to cause tissue toxicity. In contrast, the aminoindanes described by Aberg et al. were found to be useful as local or dermal anesthetics.

While various local anesthetic compounds are known in the art, there remains a need to provide for additional local anesthetic compounds that readily penetrate tissue without causing tissue toxicity, and for providing local anesthetic compounds having a long duration of action. The above needs are met by the compounds described herein.

The present invention describes the S-isomer of compounds of Formula I as described above. Specifically, the present invention describes S-2-{2-[N-(2-indanyl)-N-phenylamino]ethyl}piperidine [S-LAC-34] the free base, polymorphs, metabolites, derivatives, pharmaceutically acceptable salts and mixtures thereof. S-LAC-34 refers to the S-enantiomer of the racemic compound RS-2-{2-[N-(2-indanyl)-N-phenylamino]ethyl}piperidine. S-LAC-34 has the formula:

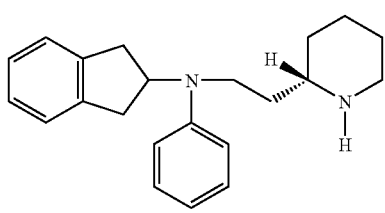

S-2-{2-[N-(2-indanyl)-N-phenylamino]
ethyl}piperidine [S-LAC-34]

Isomerism refers to the phenomenon where two compounds have identical chemical structure, i.e., have the same order of attachment of individual atoms, but differ in spatial configuration of the atoms. The spatial configuration of the atoms is usually determined by the use of X-ray crystallography or by known stereo specific synthetic transformations. Once known, the spatial configuration is labeled with symbols "R" or "S" according to the Cahn, Ingold, and Prelog system. Under the system, the atoms or groups surrounding an asymmetric center are given priorities according to atomic number and various sequence considerations. Then, the molecule is rotated so that the group with lowest priority is away from the viewer. Finally, it is observed whether the atoms in the descending order of priority form the clockwise or counterclockwise motion. If the motion is clockwise, the configuration is labeled "R" and the compound is referred to as an S-isomer. If the motion is counterclockwise, the configuration is labeled "S" and the compound is referred as an S-isomer.

As actions of pharmaceutical compounds may be the result of interacting with biological receptors, and the biological receptors may be stereo selective, R and S isomers may possess different pharmacological activities and effects upon administration to a subject. For example, one of the isomers may be more potent (require a smaller dose to reach a desired effect). Similarly, one of the isomers may have a faster onset of action and/or a longer duration of action. Further, one of the isomers may have lower incidents of adverse effects.

The racemic compound, RS-LAC-34, has been shown to be an active local anesthetic compound, particularly useful for dermal anesthesia (U.S. Pat. No. 6,413,987). It has now been found that S-LAC-34 differs significantly from the racemate and R-LAC-34. S-LAC-34 has a longer duration of action than both the racemate and the S-isomer. Furthermore, while suitable for use as a local anesthetic, the S-isomer expresses analgesic activity and may therefore be effective for treating pain. The S-isomer also has low dermal toxicity and may be combined with a vasoconstrictor to obtain an even more prolonged duration of local anesthesia.

OBJECT AND SUMMARY OF THE INVENTION

It is an object of the invention to provide for the S-isomer of compounds of Formula I.

It is another object of the invention to provide for pharmaceutical formulations containing the S-isomer of compounds of Formula I, the free base, polymorphs, derivatives, metabolites, pharmaceutically acceptable salts and mixtures thereof.

It is a further object of the present invention to provide compositions and methods for providing local anesthesia by administering to a discrete site in a patient a therapeutically effective amount of the S-isomer of Formula I for inducing anesthesia.

It is another object of the present invention to provide compositions and methods for providing pain relief in a patient by administering a therapeutically effective amount of the S-isomer of compounds of Formula I to a discrete site in a patient for the treatment of acute or chronic pain, nociceptive and neuropathic pain, pre- and post-operative pain, cancer pain, pain associated with neurotransmitter dysregulation syndromes and orthopedic pain.

It is another object of the invention to provide compositions and methods for improving sleep behavior in a patient by administering a therapeutically effective amount of the S-isomer of compounds of Formula I to a discrete site in a patient in need of pain relief, thereby alleviating the pain and improving the sleep of the patient.

It is an object of the present invention to provide the S-isomer of 2-{2-[N-(2-indanyl)-N-phenylamino]ethyl}piperidine (S-LAC-34).

It is another object of the present invention to provide pharmaceutical formulations containing S-LAC-34, the free base, polymorphs, derivatives, metabolites, pharmaceutically acceptable salt and mixtures thereof.

It is a further object of the present invention to provide compositions and methods for providing local anesthesia by administering to a discrete site in a patient a therapeutically effective amount of S-LAC-34 for inducing anesthesia.

It is another object of the present invention to provide compositions and methods for providing pain relief in a patient by administering a therapeutically effective amount of S-LAC-34 to a discrete site in a patient for the treatment of acute or chronic pain, nociceptive and neuropathic pain, pre- and post-operative pain, cancer pain, pain associated with neurotransmitter dysregulation syndromes and orthopedic pain.

It is another object of the invention to provide compositions and methods for improving sleep behavior in a patient by administering a therapeutically effective amount of S-LAC-34 to a discrete site in a patient in need of pain relief, thereby alleviating the pain and improving the sleep of the patient.

It is a further object of present invention to provide processes for the preparation of S-LAC-34.

In accordance with the above objects and others, in certain embodiments of the present invention there is provided the S-isomer of the formula:

Formula I

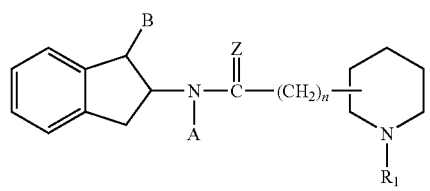

or a pharmaceutically acceptable salt, base, or mixture thereof, wherein n is equal to 0, 1, 2, or 3, Z represents two hydrogen atoms or an oxygen atom, the $(CH_2)_n$ group having a straight or branched chain, B represents hydrogen, an alkoxy radical containing 1 to 3 carbon atoms or a group of the formula

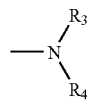

in which $R_3$ and R4 may independently be selected from the group consisting of methoxy, ethoxy, a lower alkyl or hydroxyalkyl radical containing 1 to 3 carbon atoms, whereby $R_3$ may also represent hydrogen, A is a 2-pyridyl radical, an unsubstituted phenyl radical or a phenyl radical substituted by at least one substituent in the ortho, meta and/or para position, and $R_1$ represents a hydrogen, or a lower alkyl or hydroxyalkyl containing 1 to 4 carbon atoms and the piperidine nucleus is attached at the 2-, 3-, or 4-position, wherein the compound is useful for inducing anesthesia and analgesia in a patient in need thereof, the compound having a long duration of action when administered to a patient.

In accordance with the above objects and others, in certain embodiments of the present invention there is also provided S-LAC-34 having the formula:

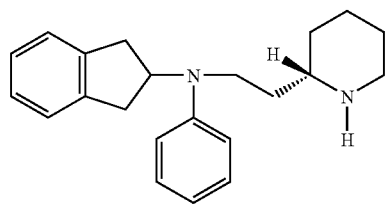

or a free base, pharmaceutically acceptable salt, polymorph or mixture thereof, wherein the compound is useful for inducing anesthesia and analgesia in a patient in need thereof, the compound having a long duration of action when administered to a patient.

In certain embodiments, there is provided a substantially pure S-isomer of the compounds described herein. The compounds contain substantially pure S-isomer when the compound is 95% or more S-isomer. In other embodiments, the compounds contain 97% or more S-isomer. In yet another embodiment, the compounds contain 99% or more S-isomer.

In certain embodiments, a substantially pure S-2-{2-[N-(2-indanyl)-N-phenylamino]ethyl}piperidine is provided. Substantially pure S-2-{2-[N-(2-indanyl)-N-phenylamino]ethyl}piperidine contains 95% or more S-2-{2-[N-(2-indanyl)-N-phenylamino]ethyl}piperidine. In other embodiments, substantially pure S-2-{2-[N-(2-indanyl)-N-phenylamino]ethyl}piperidine contains 97% or more S-2-{2-[N-(2-indanyl)-N-phenylamino]ethyl}piperidine. In yet another embodiment, substantially pure S-2-{2-[N-(2-indanyl)-N-phenylamino]ethyl}piperidine contains 99% or more S-2-{2-[N-(2-indanyl)-N-phenylamino]ethyl}piperidine.

In certain embodiments, there is provided a pharmaceutical formulation for providing anesthesia and analgesia in a patient in need thereof comprising a therapeutically effective amount of a compound of formula 1 and a pharmaceutically acceptable excipient.

In other embodiments, the pharmaceutical formulation contains substantially pure S-2-{2-[N-(2-indanyl)-N-phenylamino]ethyl}piperidine (S-LAC-34) and a pharmaceutically acceptable excipient.

The S-isomer of the compounds of the present invention, e.g., S-LAC-34, may be useful for providing local anesthesia to a patient in need thereof. In particular, it may be useful for providing topical anesthesia, dermal anesthesia, ocular anesthesia, mucosal anesthesia, intravenous regional anesthesia, infiltration anesthesia, field block anesthesia, and nerve block anesthesia. Infiltration anesthesia and nerve blocks include epidural anesthesia, spinal anesthesia, dental anesthesia and peripheral nerve blocks. Dermal anesthesia comprises anesthesia, for example, for the removal of lentigens, for skin grafts or for sunburns. Topical mucosal anesthesia comprises local anesthesia by topical application or by topical injections of any accessible mucous membrane, such as for example those of the eye, mouth, the ear-nose-throat, the rectal area and the uro-genital tract.

Of particular interest is the use of the compounds in dentistry, where infiltration anesthesia of the lower jaw may be achieved because of the outstanding ability of the compound to penetrate biological tissues; presently infiltration anesthesia is used for the upper jaw, while mandibular nerve blocks have to be used for the lower jaw, where the bone structure is of high density.

When used as a topical anesthetic to eliminate pain from hemorrhoids, the long duration of the relief may be of special importance, as is the lack of unwanted effects on wound healing.

The compounds herein may be of particular importance for use in dermal anesthesia, wherein a longer duration of dermal anesthesia is sought.

In certain embodiments, there is provided a method of inducing anesthesia in a patient in need thereof, comprising administering to a discrete site in a patient in need thereof an anesthetic inducing amount of a substantially pure S-isomer of a compound of formula I. In certain embodiments, the substantially pure isomer is S-2-{2-[N-(2-indanyl)-N-phenylamino]ethyl}piperidine (S-LAC-34), wherein the S-2-{2-[N-(2-indanyl)-N-phenylamino]ethyl}piperidine (S-LAC-34) provides an immediate anesthetic effect when administered to the discrete site.

The compounds described herein may also be useful for providing analgesia to a patient in need thereof for relieving pain such as acute or chronic pain, nociceptive pain (pain transmitted across intact neuronal pathways), neuropathic pain (pain caused by damage to neural structures), pain from nerve injury (neuromas and neuromas in continuity), pain from neuralgia (pain originating from disease and/or inflammation of nerves), pain from myalgias (pain originating from disease and/or inflammation of muscle), pain associated with painful trigger points, pain from tumors in soft tissues, pain associated with neurotransmitter-dysregulation syndromes (disruptions in quantity/quality of neurotransmitter molecules associated with signal transmission in normal nerves) and pain associated with orthopedic disorders such as conditions of the foot, knee, hip, spine, shoulders, elbow, hand, head and neck.

In certain embodiments, there is provided a method of providing analgesia or alleviating pain in a patient in need thereof, comprising administering to a discrete site in a patient in need thereof an analgesic effective amount of a substantially pure isomer of a compound of Formula I. In certain embodiments, the substantially pure isomer is S-2-{2-[N-(2-indanyl)-N-phenylamino]ethyl}piperidine (S-LAC-34), wherein the S-2-{2-[N-(2-indanyl)-N-phenylamino]ethyl}piperidine (S-LAC-34) provides a longer duration of analgesic effect when administered to the discrete site.

In other embodiments, the S-isomers of the compounds described herein, may be useful for improving sleep behavior (patterns), whereby treatment of the underlying pain or painful condition allows a patient to have improved sleep.

In certain embodiments, there is provided a method of improving sleep in a patient in need thereof, comprising administering to a discrete site in a patient in need thereof an analgesic effective amount of a substantially pure S-isomer of Formula I. In another embodiment, the substantially pure S-isomer is S-2-{2-[N-(2-indanyl)-N-phenylamino]ethyl}piperidine (S-LAC-34), wherein the S-2-{2-[N-(2-indanyl)-N-phenylamino]ethyl}piperidine (S-LAC-34) alleviates pain experienced by the patient and provides for improved sleep resulting from the alleviation of pain.

In other embodiments, S-isomer of the compounds of the invention may be useful for treating various other conditions such as hemorrhoids, arrhythmias, convulsions, hiccups and can be used to inhibit sodium and potassium ion fluxes over cell membranes in the body.

The pharmacological effects of the S-isomer of the compounds described herein may provide a longer duration of action, thus making the S-isomer a pharmaceutically effective treatment for inducing a prolonged anesthetic effect and/or providing prolonged analgesia in an acute setting. The long duration of action may also make the compounds useful to treat chronic conditions such that a single dose may be administered at the onset of symptoms and provide a prolonged pharmacological effect.

In other embodiments, there is provided a process for preparing a substantially pure S-isomer of the compounds of formula I, wherein the chirality of the S-isomer is established from the beginning.

In certain embodiments, the substantially pure isomer is S-2-{2-[N-(2-indanyl)-N-phenylamino]ethyl}piperidine (S-LAC-34) which is prepared by: a) sequentially converting: i) an N-protected L-pipecolic acid to a corresponding diazomethyl ketone; ii) the diazomethyl ketone to a methyl ester; iii) the methyl ester to a primary alcohol; and iv) the primary alcohol to an alkyl halide; b) reacting the resulting S-alkyl halide with 2-(phenylamino)indane; and c) removing an N-protecting group to obtain S-2-{2-[N-(2-indanyl)-N-phenylamino]ethyl}piperidine (S-LAC-34).

In order that the invention described herein may be more fully understood, the following definitions are provided for the purposes of this disclosure:

"Patient" refers to animals, preferably mammals, more preferably humans. The term "patient" includes adults and children, and includes men and women. Children include neonates, infants, and adolescents.

The term "environmental fluid" described herein shall mean any environmental or biological fluid. For example, certain biological fluids include, but are not limited to, gastrointestinal fluid, saliva, blood, lymph fluid, cerebrospinal fluid, ocular fluid, intra-articular fluid and any other fluid of a patient.

"Acute pain" shall mean any pain that presents with a rapid onset followed by a short, severe course, e.g., headache, pain associated with cancer, fractures, strains, sprains, and dislocations of bones, joints, ligaments and tendons.

"Chronic pain" shall mean pain that lasts for a long period of time or is marked by frequent recurrence, e.g., pain associated with terminal illnesses, arthritis, autoimmune diseases; or neuropathic pain caused by degenerative diseases such as diabetes mellitus or spinal degeneration, or resulting from neural remodeling following traumatic injury or surgery.

As used herein, the term "local anesthetic" means any drug or mixture of drugs that provides local numbness and/or analgesia.

The term "prodrug" as used herein means an inactive precursor(s) of the compounds described herein that may be converted into the active form of the compound(s) in the body by normal metabolic processes.

The term "oral" administration means by mouth and gastrointestinal tract by mouth.

The term "parenteral" means intravenous, intrarterial, intracardiac, intraspinal, intraosseous, intrarticular, intrasynovial, intracutaneous, subcutaneous, and intramuscular by injection, implantation or infiltration.

The term "injection" shall mean administration to a discrete site through the skin or into tissue of a human or animal.

The term "implantation" shall mean administration to a discrete site by embedding the dose of compound into the skin, tissue, muscles, tendons, joints, or other body parts of a human or animal.

The term "infiltration" shall mean administration into a discrete injection site, or surgical site or open wound.

The term "topical anesthesia" is in this document defined as local anesthesia of mucosal membranes, such as for examples those of the eye, the ear, the mouth, the nose, the rectal area and the urogenital tract.

The term "dermal anesthesia" is in this document defined as local anesthesia of the skin.

"Infiltration anesthesia" and "nerve blocks" of afferent or efferent nerves are in this document called "local anesthesia".

The term "ocular" administration means conjunctival, corneal, and intraocular administration.

By co-administration it is meant either the administration of a single composition containing both the compound and an additional therapeutically effective agent(s), e.g., local anesthetic or phenol, or the administration of the compound and the additional therapeutically effective agent(s) as separate compositions within short enough time periods that the effective result is equivalent to that obtained when both compounds are administered as a single composition.

The term "substantially pure isomer" means containing 95% or more of the target isomer and no more than 5% other impurities, which may include other isomers of the desired compound, e.g., S-isomer.

The term "capsaicinoid" as used herein means capsaicin, capsaicin USP and purified capsaicin, capsaicin analogues and derivatives thereof (collectively referred to as capsaicinoids in this specification and appended claims) that act at the same pharmacologic sites, e.g., VR1, as capsaicin, unless otherwise specified.

The term "long duration of action" means a prolonged pharmacological effect, e.g., anesthesia or analgesia, upon administration of the compounds to a discrete site. For purposes of the present invention, "prolonged duration of action" is further defined as producing a pharmacological effect that is longer in comparison to lidocaine, the racemate of LAC-34 and the S-Isomer of LAC-34 when administered at the same concentration.

The term "therapeutically effective amount" means an amount of compound/active agent, whereby a desired effect is obtained, e.g., induction of anesthesia or attenuation/relief from pain.

BRIEF DESCRIPTION OF THE DRAWINGS

FIG. 1 shows dermal anesthetic effects of the enantiomers of LAC-34. The onset of dermal anesthetic activity was significantly shorter for R-LAC-34 (score 3.5 after 30 min application) than for S-LAC-34 (score 2.6).

DETAILED DESCRIPTION OF THE INVENTION

The compounds of the present invention are substantially pure S-isomers of the general formula I:

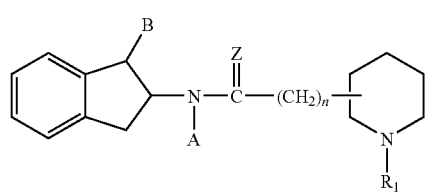

Formula I or a pharmaceutically acceptable salt, base, or mixture thereof, wherein n is equal to 0, 1, 2, or 3, Z represents two hydrogen atoms or an oxygen atom, the $(CH_2)_n$ group having a straight or branched chain, B represents hydrogen, an alkoxy radical containing 1 to 3 carbon atoms or a group of the formula

in which $R_3$ and R4 may independently be selected from the group consisting of methoxy, ethoxy, a lower alkyl or hydroxyalkyl radical containing 1 to 3 carbon atoms, whereby $R_3$ may also represent hydrogen, A is a 2-pyridyl radical, an unsubstituted phenyl radical or a phenyl radical substituted by at least one substituent in the ortho, meta and/or para position, and $R_1$ represents a hydrogen, or a lower alkyl or hydroxyalkyl containing 1 to 4 carbon atoms and the piperidine nucleus is attached at the 2-, 3-, or 4- position.

In certain preferred embodiments, the compound is an S-isomer of 2-{2-[N-(2-indanyl)-N-phenylamino]ethyl}piperidine [S-LAC-34] having the following formula:

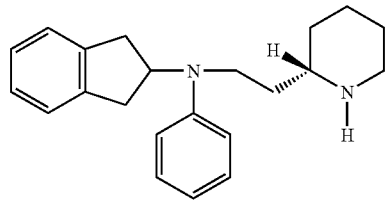

S-2-{2-[N-(2-indanyl)-N-phenylamino]ethyl}piperidine [S-LAC-34]

The compounds described herein may be the free base, a polymorph(s), a metabolite, a derivative(s), a pharmaceutically acceptable salt or mixtures thereof.

The compounds have local and dermal anesthetic activities, characterized by a longer duration of activity, e.g., time for dermal anesthetic activity, thereby making it possible to obtain long duration without the use of a vasoconstrictor, such as epinephrine, in the local anesthetic formulation. This property distinguishes the S-isomer apart from other known local anesthetic compounds—including the racemic mixture and R-isomer, e.g., R-LAC-34, which has a shorter onset of action and a shorter duration of action—and opens the possibility of using this optically active local anesthetic agent in ways that have not been possible for prior generations of local anesthetics. Comparisons of the two enantiomers of RS-LAC-34 show that S-LAC-34 demonstrates a longer duration of anesthesia than the racemic mixture or the R-isomer (R-LAC-34), which indicates unique biological effects. The compound S-LAC-34 has low dermal toxicity and can be combined with a vasoconstrictor to obtain an even more prolonged duration of local anesthesia. These unique properties are believed to be present with the S-isomers of the compounds of Formula I as well.

Administration of the Compounds

All compositions containing the compounds of the invention may be manufactured in different dosage units, suitable for administration under specific circumstances.

Suitable methods for administration of may include, but are not limited to, oral, sublingual, parenteral, rectal, urogenital, ocular, and topical administration. In clinical use, the compounds of the invention may be administered in combination with a pharmaceutically acceptable excipient (carrier), either as the free base, as a pharmaceutically acceptable, non-toxic acid addition salt.

The invention disclosed herein is meant to encompass all pharmaceutically acceptable salts thereof of the disclosed compounds. The pharmaceutically acceptable salts include, but are not limited to: i) metal salts such as aluminum, cesium, lithium, potassium, sodium, zinc salts, and the like; ii) alkaline earth metals salts such as calcium, magnesium salts, and the like; iii) organic amine salts such as dicyclohexylamine, diethylamine, ethanolamine, pyridine, picoline, triethylamine, triethanolamine, and N,N'-dibenzylethylenediamine salts, and the like; iv) inorganic acid salts such as acetate, bicarbonate, hydrochloride (mono- and dihydrochloride), hydrobromide, hydroiodide, mesylate, besylate, lactate, nitrate, sulfate, bisulfate, acid phosphate, phosphate salts, sulfonate, and the like; v) organic acid salts such as acetate, adipate, alginate, aspartate, ascorbate, citrate, benzate, besylate, butyrate salt, bitartrate, camphorate, camphor sulfonate, digluconate, formate, fumarate, glutarate, gluconate, glucoronate, gentisinate, glycerophosphate, hemisulfate, heptanoate, hexanoate, lactate, p-hydroxybenzoate, p-methoxybenzoate, hydoxynaptoicoate, isonicotinate, pantothenate, oxalate, palmitoate, pectinate, persulfate, 3-phenylpropionate, picrate, pivalate, propionate, salicylate, succinate, undecanoate, pamoate, saccharate, trifluoroacetate, thiocyanate, maleate, tartrate salts, and the like; sulfonates salts such as methanesulfonate, ethanesulfonate, 2-hydroxyehansulfonate (isothionate), 2-naphthalene sulfonate, benzenesulfonate, bisulfate, toluenesulfonate (including p-toluenesulfonate) salts, and the like; vi) amino acid salts such as arginate, asparginate, glutamate salts and the like.

In certain embodiments, the compounds may be suitable for parenteral administration. The compounds may be administered parenterally by intravenous, intraarterial, intracardiac, intraspinsal, intraosseous, intraarticular, intrasynovial, subcutaneous or intramuscular injection, implantation, infiltration or infusion.

In certain preferred embodiments, the compounds may be administered parenterally via intradermal injection.

When S-LAC-34 is administered parenterally, in certain embodiments, the compound may be administered alone or together with a pharmaceutically acceptable and physiological acceptable excipients, e.g., diluent, for parenteral administration. Solutions for parenteral administration (e.g., injection or infusion) may be prepared as aqueous solutions of a water soluble, pharmaceutically acceptable salt of the active compound, such as for example the dihydrochloride salt in a concentration from 0.1% to 3.0%.

Suitable diluents for parenteral administration include, but are not limited to: aqueous vehicles, nonaqueous vehicles, antimicrobial agents, isotonic agents, buffers, antioxidants, suspending and dispersing agents, emulsifying agents, sequestering or chelating agents and any combinations or mixtures thereof. Examples of aqueous vehicles preferably include Sodium Chloride Injection, Bacteriostatic Sodium Chloride Injection, Ringers Injection, Isotonic Dextrose Injection, Sterile Water Injection, Bacteriostatic Sterile Water Injection, Dextrose Lactated Ringers Injection and any combinations or mixtures thereof. Nonaqueous parenteral vehicles preferably include fixed oils of vegetable origin, cottonseed oil, corn oil, sesame oil, peanut oil and any combinations or mixtures thereof. Antimicrobial agents in bacteriostatic or fungistatic concentrations preferably include phenols, cresols, mercurials, benzyl alcohol, chlorobutanol, ethyl and propyl p-hydroxybenzoic acid esters, thimerosal, benzalkonium chloride benzethonium chloride and mixtures thereof. Isotonic agents preferably include sodium chloride, dextrose and any combinations or mixtures thereof. Buffers preferably include acetate, phosphate, citrate and any combinations or mixtures thereof. Antioxidants preferably include ascorbic acid, sodium bisulfate and any combinations or mixtures thereof. Suspending and dispersing agents preferably include sodium carboxymethylcelluose, hydroxypropyl methylcellulose, polyvinylpyrrolidone and any combinations or mixtures thereof. Emulsifying agents preferably include Polysorbate 80 (Tween 80). Sequestering or chelating agents of metal ions preferably include ethylenediaminetetraacetic acid. Additional pharmaceutically acceptable vehicles also preferably include ethyl alcohol, polyethylene glycol, glycerin, propylene carbonate and propylene glycol for water miscible vehicles and sodium hydroxide, hydrochloric acid, citric acid or lactic acid for pH adjustment and any combinations or mixtures thereof.

Depending on the pharmaceutically acceptable vehicle chosen, the compounds may be administered as an aqueous solution or suspension for injection, implantation or infiltration. Injections are separated into five distinct types, generally classified as (i) medicaments or solutions or emulsions suitable for injection; (ii) dry solids or liquid concentrates containing no buffers, diluents, or other added substances, and which upon the addition of suitable vehicles, yield solutions conforming in all aspects to the requirements for injections; (iii) preparations as described in (ii) except that they contain one or more buffers, diluents or other added substances; (iv) solids which are suspended in a suitable fluid medium and which are not to be injected intravenously or into the spinal canal; and (v) dry solids, which upon the addition of suitable vehicles, yield preparations conforming in all respects to the requirements of Sterile Suspensions (see: H. C. Ansel, Introduction to Pharmaceutical Dosage Forms, 4th Edit., 1985, pg. 238).

In certain other embodiments, a surfactant can preferably be combined with one or more of the pharmaceutically acceptable vehicles previously described herein so that the surfactant or buffering agent prevents the initial stinging or burning discomfort that may be associated with administration of the compounds described herein.

Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate),-lecithin pharmaceutical acceptable salts thereof and combinations thereof. When one or more surfactants are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%.

Buffering agents may also be used to provide drug stability; to control the therapeutic activity of the drug substance (Ansel, Howard C., "Introduction to Pharmaceutical Dosage Forms," 4.sup.th Ed., 1985); and/or to prevent the initial stinging or burning discomfort that may also be associated with administration of the compounds described herein. Suitable buffers include, but are not limited to sodium bicarbonate, sodium citrate, citric acid, sodium phosphate, pharmaceutically acceptable salts thereof and combinations thereof.

When one or more buffers are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%.

In certain preferred embodiments, the pharmaceutical vehicle utilized to deliver the compounds by injection may comprise about 20% PEG 300, about 10 mM histidine and about 5% sucrose in water for injection.

The percentage of the compounds described herein contained in a pharmaceutically acceptable formulation for parenteral administration may vary. In certain embodiments, the compounds may be present in a formulation in an amount to provide for about 0.001% to about 25% by weight of the compound. In other embodiments, the compounds may be present in a formulation in an amount to provide for a about 0.05% to about 10% by weight of the compound. In yet another embodiment, the compounds may be present in a formulation in an amount to provide for a 0.1% to about 5% by weight of the compound. In other embodiments, the amount of compound may range from about 0.1% to about 3% by weight for injections or from about 0.05% to 3% by weight for infusions (e.g., for epidural, spinal or regional anesthesia). In yet another embodiment, the compounds may be present in an amount from about 0.1% to about 10% by weight for preparations for dermal anesthesia.

Formulations for parenteral administration may contain the compound as a free base or water-soluble salt, such as for example the di-hydrochloride salt.

If parenteral administration is not viable or another form of administration is desired, the compounds may be administered topically or transdermally by known methods. In certain embodiments, the compounds may be administered as a cream, ointment, emollient, paste, gel, solution, suspension, liposome, aerosol or spray. In certain embodiments, the compounds may be administered in a transdermal patch. In other embodiments, an occlusive dressing may be placed over the area where the compound is topically applied.

Topical administration includes, but is not limited to, epicutaneous, transdermal, conjunctival, intraocular, intranasal, intrarespiratory, aural, mucosal, rectal, vaginal, and urethral administration.

While the various salt forms of the compounds are useful in dermal anesthesia, dermal formulations containing the free base may be preferred.

The topical formulations and/or transdermal therapeutic systems of the present invention may include at least one excipient such as a penetration enhancer, anti-oxidant, stabilizer, carrier, or vehicle.

In certain embodiments of the present invention, wherein the topical formulation further includes a penetration enhancer composition, the amount of enhancer composition present in the formulation will depend on a number of factors, e.g., the strength of the particular enhancer composition, the desired increase in skin permeability, and the amount of drug which is necessary to deliver.

Suitable enhancers include, but are not limited to, dimethylsulfoxide (DMSO), N,N-dimethylacetamide (DMA), decylmethylsulfoxide ($C_{10}$ MSO), polyethylene glycol monolaurate (PEGML), propylene glycol (PG), PGML, glycerol monolaurate (GML), polyoxyethylene fatty acid esters, lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in U.S. Pat. No. 5,229,130 to Sharma. Such oils include, for example, safflower oil, cotton seed oil and corn oil.

Additional enhancers for use in conjunction with the present invention are lipophilic compounds having the formula [RCOO]$_n$R', wherein n is 1 or 2 and R is $C_1$-$C_{16}$ alkyl optionally substituted with 1 or 2 hydroxyl groups, and R' is hydrogen or $C_1$-$C_{16}$ alkyl optionally substituted with 1 or 2 hydroxyl groups. Within this group, a first subset of compounds are represented by the formula [CH$_3$(CH$_2$)$_m$COO]$_n$R' in which m is an integer in the range of 8 to 16, n is 1 or 2, and R' is a lower alkyl ($C_1$-$C_3$) residue that is either unsubstituted or substituted with one or two hydroxyl groups. Preferred enhancers within this group include an ester which is a lower alkyl ($C_1$-$C_3$) laurate (i.e., m is 10 and n is 1) such as "PGML". It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula CH$_3$(CH$_2$)$_m$—O—CO—CHR$_1$R$_2$, in which R$_1$ and R$_2$ are independently hydrogen, hydroxyl, or lower alkyl ($C_1$-$C_3$), and m is as above. Particularly preferred enhancers within this group are lauryl lactate and myristyl lactate. In addition, a third subset of compounds within this group are analogous fatty acids, i.e., acids having the structural formula CH$_3$(CH$_2$)$_m$COOH where m is as above. A particularly preferred acid is lauric acid.

Other enhancer compositions are wherein a lipophilic compound as just described, particularly PGML is combined with a hydrophilic compound, such as a $C_2$-$C_6$ alkanediol. One preferred hydrophilic enhancer within this group is 1,3-butanediol. Such enhancer compositions are described in detail in PCT Publication No. WO 95/05137, published Feb. 23, 1995, herein incorporated by reference. Another hydrophilic enhancer that may be included in these compositions is an ether selected from the group consisting of diethylene glycol monoethyl ether (Transcutol®) and diethylene glycol monomethyl ether. Such enhancer compositions are described in detail in U.S. Pat. Nos. 5,053,227 and 5,059,426 to Chiang et al., the disclosures of which are herein incorporated by reference.

Other enhancer compositions may include mixture or combinations of any of the aforementioned enhancers, and the like.

In certain embodiments the topical formulation may include at least one water-insoluble, pharmacologically approved, cellulose, such as alkyl cellulose or hydroxyalkyl cellulose, and the like. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as oleic acid and myristyl may be used in combination with the cellulose derivative.

In certain embodiments, the topical formulation may further include hydrocarbons such as liquid paraffin, vaseline, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like.

In certain embodiments, the topical formulation may further include emulsifiers and dispersing agents which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain embodiments of the present invention, the topical formulation may include a gelling agent such as methylcellulose, ethylcellulose, hydroxyethylcellulose, hydroxypropyl-cellulose, hydroxypropylmethylcellulose, carboxymethylcellulose, carbomer, and the like.

The topical formulation may further include one or more antimicrobial agents, preservatives, buffers, stabilizers, surfactants or anti-oxidants.

Examples of preservatives that may be used in a formulation according to the present invention include, but are not limited to, bacteriostatic compounds and other preservatives suitable for topical administration including various alcohols, sorbic acid and salts and derivatives thereof, ethylenediamine, monothioglycerol, and thimerosal.

Examples of stabilizers that may be present in a formulation according to the present invention include pH buffers suitable for topical administration, complexing agents, chelating agents and the like.

Examples of anti-oxidants that may be used in a formulation according to the present invention include ascorbic acid and its derivatives, e.g., ascorbyl palmitate, as well as butylated hydroxyanisole, butylated hydroxytoluene, sodium bisulfite, sodium metabisulfite, and others.

Other excipients that may be included in the drug formulation include carriers, thickening agents (e.g. carboxypolymethylene), pH-adjusting agents (e.g. sodium hydroxide), preservatives, tackifiers, pigments, dyes, and other additives that do not adversely affect the mechanical or adhesive properties of the formulation. "Carriers" or "vehicles" as used herein refer to carrier materials suitable for transdermal drug administration, and include any such materials known in the art, e.g., any liquid, gel, emulsion, solvent, liquid diluent, solubilizer, or the like, which is nontoxic and which does not interact with other components of the composition in a deleterious manner. The term "carrier" or "vehicle" as used herein may also refer to stabilizers, crystallization inhibitors, dispersing agents or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

Carrier materials suitable for use in the instant compositions include those well-known for use in the cosmetic and medical arts as bases for ointments, lotions, salves, aerosols, suppositories and the like. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers herein include for example alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

In certain embodiments, excipients such as mineral oil and capric/caprylic triglycerides may be used as the oil phase for emollients or emulsions.

The combination of excipients provides means of delivering the drug from supersaturated compositions through skin where the penetration barriers are decreased, while the formulations also are repairing barrier damage, protecting the skin, and hydrating the skin.

The topical and/or transdermal composition may contain one or more active compounds and the compounds may be prepared as bases or salts to facilitate dermal penetration.

The topical or transdermal formulations of the present invention may be formulated in a manner such that the percentage of compound contained in the formulation ranges from about 0.001% to about 25% by weight. In certain embodiments, the compound may be present in a formulation in an amount from about 0.01% to about 10% by weight. In yet another embodiment, the compound may be present in a formulation in an amount from about 0.1% to about 5% by weight. In yet another embodiment, the compound may be present in an amount from about 0.1% to about 10% by weight for preparations for topical mucosal anesthesia or from about 0.05% to about 2.5% by weight in preparations for use on mucous membranes.

The compounds of the present invention may also be formulated into a suitable ophthalmic preparation. In certain embodiments, the ophthalmic preparation may contain additional active agents such as, but not limited to, an antibiotic, a vasoconstrictor, a vasodilator, a glucocorticosteroid, an antiseptic and/or bacteriostatic agent.

The compounds may be formulated into suitable dosage forms for rectal or vaginal administration. Dosage units for rectal or vaginal administration may be prepared in the form of ointments or suppositories, which may contain the active substance in a mixture with a neutral fat base, or they may be prepared in the form of gelatin-rectal or vaginal capsules that contain the compound in a mixture with for example a vegetable oil or paraffin oil. Ointments, suppositories or creams containing the compound may be useful for the treatment of hemorrhoids. In certain embodiments, co-administration of the S-LAC-34 with a vasoconstrictor may be particularly useful for the treatment of hemorrhoids.

Delivery systems can also be used to administer the compounds of the present invention. The delivery systems may produce modality-specific blockade, as reported by Schneider, et al., Anesthesiology, 74:270-281 (1991), or possess physical-chemical attributes that make them more useful for sustained release then for single injection blockade, as reported by Masters, et al., Soc. Neurosci. Abstr., 18:200 (1992), the teachings of which are incorporated herein. An example of a delivery system includes microspheres wherein the compound may be incorporated into a polymer matrix in a percent loading of 0.1% to 90% by weight, preferably 5% to 75% by weight. It is possible to tailor a system to deliver a specified loading and subsequent maintenance dose by manipulating the percent of the compound incorporated in the polymer and the shape of the matrix, in addition to the form of local anesthetic (free base versus salt) and the method of production. The amount of compound released per day increases proportionately with the percentage of compound incorporated into the matrix (for example, from 5 to 10 to 20%).

The delivery systems are most preferably formed of a synthetic biodegradable polymer, although other materials may also be used to formulate the delivery systems, including proteins, polysaccharides, and non-biodegradable synthetic polymers. It is most preferable that the polymer degrade in vivo over a period of less than a year, with at least 50% of the polymer degrading within six months or less. Even more preferably, the polymer will degrade significantly within a month, with at least 50% of the polymer degrading into non-toxic residues which are removed by the body, and 100% of the compound being released within a two week period. Polymers should also preferably degrade by hydrolysis by surface erosion, rather than by bulk erosion, so that release is not only sustained but also linear. Polymers which meet this criteria include some of the polyanhydrides, poly(hydroxy acids) such as co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid. Polylactic acid is not useful since it takes at least one year to degrade in vivo. The polymers should be biocompatible. Biocompatibility is enhanced by recrystallization of either the monomers forming the polymer and/or the polymer using standard techniques.

Other local carrier or release systems can also be used, for example, the lecithin microdroplets or liposomes of Haynes, et al., Anesthesiology 63, 490-499 (1985), or the polymer-phospholipid microparticles of U.S. Pat. No. 5,188,837 (Domb), the disclosure of which is hereby incorporated by reference.

The delivery systems may be in the form of microparticles (e.g., microcapsules and microspheres), beads, pellets, and rods. When the delivery systems contemplate the use of microparticles, the microparticles may be in a size and distribution range suitable for implantation, injection or infiltration. The diameter and shape of the microparticles can be manipulated to modify the release characteristics. For example, larger diameter microparticles will typically provide slower rates of release and reduced tissue penetration and smaller diameters of microparticles will produce the opposite effects, relative to microparticles of different mean diameter, but of the same composition. In addition, other particle shapes, such as cylindrical shapes, can also modify release rates by virtue of the increased ratio of surface area to mass inherent to such alternative geometrical shapes, relative to a spherical shape. The diameter of microparticles may range in size from about 5 microns to about 200 microns in diameter.

In another embodiment, the microparticles may range in diameter from about 20 to about 120 microns. In another embodiment of the present invention, the compounds can be administered in the form of implantable pellets, rods and slabs. Methods for manufacture of microparticles, pellets, rods and slabs are well known in the art and include solvent evaporation, phase separation and fluidized bed coating.

Methods of Treatment

The compound of the invention may be used to provide topical anesthesia, dermal anesthesia, ocular anesthesia, intravenous regional anesthesia, infiltration anesthesia, field block anesthesia, spinal anesthesia and nerve block anesthesia.

The compounds may also be used for treating various disease states and conditions. In certain embodiments, the compounds may be useful for providing anesthesia to a patient in need thereof by administering the compound to a specific site, e.g., surgical site or open wound. In certain embodiments, the compound may be used for providing local anesthesia for minor procedures and before, during and after surgery. For example, it is contemplated that the compounds, e.g., S-LAC-34, may be used for dental procedures, plastic surgery, arthroscopic procedures, laparoscopic procedures and orthopedic procedures to name a few. In certain embodiments the compounds may be used for laparoscopic cholecystectomy, hernia repair, bunionectomy, knee replacement surgery, median sternotomy, and mastectomy.

The compounds may also express analgesic activities. In certain embodiments, the compounds may be useful for providing analgesia to a patient in need thereof to treat a painful condition. Conditions associated with pain include, but are not limited to, nociceptive pain (pain transmitted across intact neuronal pathways), neuropathic pain (pain caused by damage to neural structures), pain from nerve injury (neuromas and neuromas in continuity), pain from neuralgia (pain originating from disease and/or inflammation of nerves), pain from myalgias (pain originating from disease and/or inflammation of muscle), pain associated with painful trigger points, pain from tumors in soft tissues, pain associated with neurotransmitter-dysregulation syndromes (disruptions in quantity/quality of neurotransmitter molecules associated with signal transmission in normal nerves) and pain associated with orthopedic disorders such as conditions of the foot, knee, hip, spine, shoulders, elbow, hand, head and neck.

The receptors involved in pain detection are aptly enough referred to as nociceptor-receptors for noxious stimuli. These nociceptors are free nerve endings that terminate just below the skin as to detect cutaneous pain. Nociceptors are also located in tendons and joints, for detection of somatic pain and in body organs to detect visceral pain. Pain receptors are very numerous in the skin, hence pain detection here is well defined and the source of pain can be easily localized. In tendons, joints, and body organs the pain receptors are fewer. The source of pain therefore is not readily localized. Apparently, the number of nociceptors also influences the duration of the pain felt. Cutaneous pain typically is of short duration, but may be reactivated upon new impacts, while somatic and visceral pain is of longer duration. It is important to note that almost all body tissue is equipped with nociceptors. As explained above, this is an important fact, as pain has primary warning functions, for example, impinging on the well-being of the patient and thereby causing the patient to seek medical assistance. Nociceptive pain includes, but is not limited to post-operative pain, cluster headaches, dental pain, surgical pain, pain resulting from severe burns, post-partum pain, angina, genitor-urinary tract pain, pain associated with sports injuries (tendonitis, bursitis, etc.) and pain associated with joint degeneration and cystitis.

Neuropathic pain generally involves abnormalities in the nerve itself, such as degeneration of the axon or sheath. For example, in certain neuropathies the cells of the myelin sheath and/or Schwann cells may be dysfunctional, degenerative and may die, while the axon remains unaffected. Alternatively, in certain neuropathies just the axon is disturbed, and in certain neuropathies the axons and cells of the myelin sheath and/or Schwann cells are involved. Neuropathies may also be distinguished by the process by which they occur and their location (e.g. arising in the spinal cord and extending outward or vice versa). Direct injury to the nerves as well as many systemic diseases can produce this condition including AIDS/HIV, Herpes Zoster, syphilis, diabetes, and various autoimmune diseases. Neuropathic pain is often described as burning, or shooting type of pain, or tingling or itching pain and may be unrelenting in its intensity and even more debilitating than the initial injury or the disease process that induced it.

Neuropathies treatable by the methods of the present invention include: syndromes of acute ascending motor paralysis with variable disturbance of sensory function; syndromes of subacute sensorimotor paralysis; syndromes of acquired forms of chronic sensorimotor polyneuropathy; syndromes of determined forms of genetic chronic polyneuropathy; syndromes of recurrent or relapsing polyneuropathy; and syndromes of mononeuropathy or multiple neuropathies (Adams and Victor, Principles of Neurology, 4th ed., McGraw-Hill Information Services Company, p. 1036, 1989). Syndromes of acute ascending motor paralysis are selected from the group consisting of acute idiopathic polyneuritis, Landry-Guillain-Barre Syndrome, acute immune-mediated polyneuritis, infectious mononucleosis polyneuritis, hepatitis polyneuritis; diptheric polyneuropathy; porphyric polyneuropathy; toxic polyneuropathy (e.g., thallium); acute axonal polyneuropathy; acute panautonomic neuropathy; vaccinogenic, serogenic, paraneoplastic, polyarteretic and lupus polyneuropathy.

Syndromes of subacute sensorimotor paralysis are selected from the group consisting of deficiency states (e.g., beriberi, pellagra, vitamin B12); heavy metal/industrial solvent poisonings (e.g., arsenic, lead); drug overdose (e.g., isoniazid, disulfuram, vincristine, taxol, chloramphenicol); uremic polyneuropathy; diabetes; sarcoidosis; ischemic neuropathy and peripheral vascular disease; AIDS; and radiation (radiotherapy). Syndromes of chronic sensorimotor are selected from the group consisting of carcinoma, myeloma and other malignancies; paraproteinemias; uremia; beriberi (usually subacute), diabetes, hypo/hyperthyroidism; connective tissue disease; amyloidosis; leprosy and sepsis. Genetic chronic polyneuropathies are selected from the group consisting of dominant mutilating sensory neuropathy (adult); recessive mutilating sensory neuropathy (childhood); congenital insensitivity to pain; spinocerebellar degenerations, Riley Day Syndrome; Universal Anesthesia Syndrome; polyneuropathies w/metabolic disorder; and mixed sensorimotor-autonomic type polyneuropathies. Recurrent/relapsing polyneuropathy are selected from the group consisting of idiopathic polyneuritis; porphyria; chronic inflammatory polyradiculoneuropathy; mononeuritis multiplex; beriberi/drug overdose; refsum disease and tangier disease. Mono/multiple neuropathies are selected from the group consisting of pressure palsies; traumatic neuropathies (e.g., irradiationor electrical injury); serum, vaccinogenic (e.g., rabies, smallpox); herpes zoster; neoplastic infiltration; leprosy; diptheretic wound infections; migrant sensory neuropathy; shingles and post herpetic neuralgia.

Neurotransmitter-dysregulation pain syndromes, rather than involving abnormal or damaged nerves, result from normal nerves having disruptions in the quantity and/or quality of the various neurotransmitter molecules associated with signal transmission from one neuron to another. More specifically, sensory transmitters are released from the afferent nerve ending of one nerve cell and received by receptors at the afferent end of another nerve cell. They are chemical messengers which transmit the signal. There are numerous transmitters, including glutamate, serotonin, dopamine, norepinephrine, somatostatin, substance P, calcitonin gene-related peptide, cholecystokinin, opiates and saponins. Alterations in the quantity of transmitters and neuropeptide release, changes in the afferent receptor, changes of re-uptake of the transmitter and/or neuropeptides can all yield qualitative change of the neural signaling process. As a result, the aberrant signal transmission is interpreted by the body as pain. A representative neurotransmitter dysregulation syndrome that may be treated by the present invention includes fibromyalgia, which is a common condition characterized by a history of chronic generalized pain and physical exam evidence of at least 11 of 18 defined "tender point" sites in muscles and connective tissue (Wolfe et al., Arthritis Rheum 33:160-72, 1990). Commonly associated conditions include irritable bowel syndrome, headache, irritable bladder syndrome (interstitial cystitis), sleep disturbance, and fatigue (Goldenberg, Current Opinion in Rheumatology 8:113-123, 1996; Moldofsky et al., Psychosom Med 37:341-51, 1975; Wolfe et al., 1990; Wolfe et al., J Rheum 23:3, 1996; Yunus et al., Semin Arthritis Rheum 11:151-71, 1981).

A predominant theory regarding the etiology of fibromyalgia holds that an imbalance and/or dysregulation of neurotransmitter function may occur within the central nervous system (CNS), either in the brain or spinal cord and in the relation of the CNS to muscle and connective tissue via regulatory nerve pathways (Goldenberg, 1996; Russell, Rheum Dis Clin NA 15:149-167, 1989; Russell et al., J Rheumatol 19:104-9, 1992; Vaeroy et al., Pain 32:21-6, 1988; Wolfe et al., 1996). Neurotransmitters are chemical messengers, amino acids, biogenic amines and neuropeptides, emitted from nerve cells that interact with receptors on other nerve cells, as well as other cell types, including muscle and immune cells. Neurotransmitter imbalance, which leads to increased pain experience, may include a qualitative and/or quantitative decrease in the function of such neurotransmitters as glutamate, serotonin, dopamine, norepinephrine, somatostatin, substance P, calcitonin gene-related peptide, cholecystokinin, opiates and saponins. Fibromyalgia is characterized by a relative deficit of serotonin effect and relative excess of substance P effect. This imbalance results in amplified modulation of pain-signaling in the central nervous system, resulting in neurogenic pain (Matucci-Cerinic, Rheumatic Disease Clinics of North America 19:975-991, 1993; Bonica, The Management of pain, Lea and Febiger, 2d ed., Philadelphia, pp. 95-121, 1990). Similar mechanisms may be at work to cause associated conditions; for example, dysregulation of neurotransmitter signaling in the bowel musculature, leading to irritable bowel syndrome symptoms such as cramping, diarrhea, and/or constipation.

Neurotransmitter-dysregulation pain syndromes include, but are riot limited to the following: generalized syndromes, localized syndromes; craniofascial pain; vascular disease; rectal, perineum and external genitalia pain; and local syndromes of the leg/foot.

Generalized syndromes are selected from the group consisting of stump pain, causalgia, reflex sympathetic dystrophy, fibromyalgia or diffuse myofascial pain and burns. Localized syndromes are selected from the group consisting of trigeminal neuralgia; acute herpes zoster; panautonomic neuralgia; geniculate neuralgia (Romsay Hunt Syndrome); glossopharyngeal neuralgia; vagus nerve neuralgia and occipital neuralgia. Craniofacial pain includes temporomandibular pain. Suboccipital and cervical musculoskeletal disorders are selected from the group consisting of myofascial syndrome, which includes cervical sprain cervical hyperextension (whiplash); stemocleidomastoid muscle; trapezius muscle; and stylohyoid process syndrome (Eagle's syndrome). Vascular disease is selected from the group consisting of Raynaud's disease; Raynaud's phenomenon; frosbite; erythema pernio (chilblains); acrocyanosis and livedo reticularis. Rectal, perineum and external genitalia pain are selected from the group consisting of iliohypogastric neuralgia; iliolinguinal nerve; genotifemoral nerve and testicular pain. Local syndromes of the leg/foot are selected from the group consisting of lateral cutaneous neuropathy (neuralgia paresthetica); obturator neuralgia; femoral neuralgia; sciatica neuralgia; interdigital neuralgia of the foot (Morton's metatarsalgia or neurma); injection neuropathy and painful legs and moving toes.

Pain Intensity assessment scales are typically used by those of ordinary skill in the art to evaluate analgesic choices and therapeutic effects.

A Visual Analogue Scale (VAS) is a measurement instrument that measures a characteristic that is believed to range across a continuum of values and cannot easily be directly measured. For example, the amount of pain that a patient feels ranges across a continuum from none to an extreme amount of pain may be indirectly measured via the use of a VAS. Operationally a VAS is usually a horizontal line, 100 mm in length, anchored by word descriptors at each end, for example "no pain" at one end and "very severe pain" at the other end. The patient, marks on the line the point that they feel represents their perception of their current state. The VAS score is determined by measuring in millimeters from the left hand end of the line to the point that the patient marks. The 100-mm visual analog scale (VAS), a unidimensional scale that is versatile and easy to use, has been adopted in many settings.

Treatment of Chronic Post-Hemiorrhaphy Pain

In a preferred embodiment, the compounds may be used for the treatment/attenuation of chronic post-hemiorrhaphy pain. Chronic post-hemiorrhaphy pain occurs in between 5-30% of patients, with social consequences limiting some type of activity in about 10% of patients and 1-4% of patients are referred to chronic pain clinics. Nerve damage is probably the most plausible pathogenic factor, but specific principles for therapy have not been evidence-based and range from usual analgesics to re-operation with mesh removal and various types of nerve sections without any demonstrated efficacy in sufficient follow-up studies with or without randomized data. In patients suffering from pain associated with chronic post-hemiorrhaphy, a dose the compound may be administered to the site where the surgery was performed or to the immediate area surrounding the incision.

Treatment of Pain Associated with Morton's Neuroma

In another preferred embodiment, the compounds may be used for the treatment/attenuation of pain associated with Morton's Neuroma. Morton's Neuroma is considered to be most likely a mechanically induced degenerative neuropathy which has a strong predilection for the third common digital nerve in middle-aged women. It is considered a well-defined model of neuropathic pain. The usual medical treatment of Morton's neuroma includes local injection of steroids, often with lidocaine. When nonsurgical means fail to relieve patient's symptoms, surgical removal of this offending neuroma through a dorsal approach can produce dramatic relief of symptoms in approximately 80% of patients. However, 20% of patients experience neuroma recurrence (referred to as stump or amputation neuroma) that often causes more severe pain that the original neuroma and is generally treatment resistant. Administration of the compounds in accordance with the invention is useful for the treatment of the neuropathic pain associated with Morton's Neuroma and may reduce the re-occurrence of pain associated with stump or amputation neuroma.

Orthopedic Disorders

The compounds of the invention may be utilized to treat/attenuate pain associated with orthopedic disorders. Orthopedic disorders treatable via the use of the formulations and methods of the invention include but are not limited to disorders of the knee, shoulders, back, hip, spine, elbows, foot, hand and other disorders, which involve pain at a specific site or body space. Orthopedic disorders affecting these locations include, but are not limited to bursitis, tendonitis, osteoarthritis, and rheumatoid arthritis. Bursitis is the inflammation of a bursa. Bursae are saclike cavities or potential cavities that contain synovial fluid located at tissue sites where friction occurs (e.g., where tendons or muscles pass over bony prominences). Bursae facilitate normal movement, minimize friction between moving parts, and may communicate with joints. In the normal state, the bursa provides a slippery surface that has almost no friction. A problem arises when a bursa becomes inflamed. The bursa loses its gliding capabilities, and becomes more and more irritated when it is moved. When the condition called bursitis occurs, the slippery bursa sac becomes swollen and inflamed. The added bulk of the swollen bursa causes more friction within already confined spaces. Also, the smooth gliding bursa becomes gritty and rough. Movement of an inflamed bursa are painful and irritating. Bursitis usually occurs in the shoulder (subacromial or subdeltoid bursitis). Other sites include the olecranon (miners' elbow), prepatellar (housemaid's knee) or suprapatellar, retrocalcaneal (Achilles), iliopectineal (iliopsoas) of the hip, ischial (tailor's or weaver's bottom) of the pelvis, greater trochanteric of the femur, and first metatarsal head (bunion). Bursitis may be caused by trauma, chronic overuse, inflammatory arthritis (eg, gout, rheumatoid arthritis), or acute or chronic infection (eg, pyogenic organisms, particularly *Staphylococcus aureus*; tuberculous organisms; which now rarely cause bursitis). Orthopedic disorders of the foot include, but are not limited to, heel spurs, corns, bunions, Morton's neuroma, hammertoes, ankle sprain, fractures of the ankle or metatarsals or sesamoid bone or toes, plantar fascitis and injuries to the achilles tendon. Orthopedic disorders of the hand include, but are not limited to, arthritis, carpal tunnel syndrome, ganglion cysts, tendon problems such as lateral epicondylitis, medial epicondylitis, rotator cuff tendonitis, DeQuervian's tenosynovitis, and trigger finger/trigger thumb. Other orthopedic disorders include, but are not limited to, Paget's disease, scoliosis, soft-tissue injuries such as contusions, sprains and strains, long bone fractures and various other sports injuries some of which include patellar tendonitis and lumbar strain.

Treatment of non-infected acute bursitis has mainly consisted of temporary rest or immobilization and high-dose NSAIDs, sometimes narcotic analgesics, may be helpful. Voluntary movement should be increased as pain subsides. Pendulum exercises are particularly helpful for the shoulder joint. Aspiration and intrabursal injection of depot corticosteroids 0.5 to 1 ml (triamcinolone diacetate 25 or 40 mg/ml) mixed with at least 3 to 5 ml of local anesthetic after infiltration with 1% local anesthetic (e.g., lidocaine) is the treatment of choice when rest alone is inadequate. The depot corticosteroid dose and volume of mixture are gauged to the size of the bursa. Reaspiration and injection may be required with resistant inflammation. Systemic corticosteroids (prednisone 15 to 30 mg/day or equivalent for 3 days) are occasionally indicated in resistant acute cases after infection and gout have been excluded. Chronic bursitis is treated as acute bursitis, except that splinting and rest are less likely to be helpful. Surgery is rarely needed to treat bursitis and is usually done only in the chronic cases that have not improved with traditional therapy. The most common surgical treatment, if needed, is an Incision and Drainage (called an I and D) and is used only in cases of infected bursa. The surgeon first numbs the skin with an anesthetic and then opens the bursa with a scalpel. Finally, the surgeon drains the fluid present in the inflamed bursa. Sometimes it is necessary to excise the entire bursa surgically. This is indicated only if the bursal swelling causes problems.

The compound may be administered via injection in a location and fashion similar to that currently utilized with respect to localized injections of corticosteroids. For example, in certain embodiments, the dose of the compound may be administered by intra-articular injection into the bursa.

Tendonitis

The compounds of the invention may be utilized to treat/attenuate pain associated with tendonitis (inflammation of the tendons). When tendons become inflamed, the action of pulling the muscle becomes irritating and painful. The cause is often unknown. Most instances tendonitis occurs in middle-aged or older persons as the vascularity of tendons attenuates; repetitive microtrauma may increase injury. Repeated or extreme trauma (short of rupture), strain, or excessive (unaccustomed) exercise is most frequently implicated. The most common cause of tendonitis is overuse. Commonly, individuals begin an exercise program, or increase their level of exercise, and begin to experience symptoms of tendonitis. The tendon is unaccustomed to the new level of demand, and this overuse will cause an inflammation and tendonitis. Tendonitis produces pain, tenderness and stiffness near a joint which is aggravated by movement.

General practitioners commonly use non-steroidal anti-inflammatory drugs (NSAIDs) to treat tennis elbow, but there are no trials to date that have compared them with other painkillers and one study found no clinically important benefit over placebo. Symptomatic relief is provided by rest or immobilization (splint or cast) of the tendon, application of heat for chronic inflammation or cold for acute inflammation (whichever benefits the patient should be used), local analgesic drugs, and NSAEDs for 7 to 10 days. A critical review of the role of various anti-inflammatory medications in tendon disorders found limited evidence of short-term pain relief and no evidence of their effectiveness in providing even medium term clinical resolution. Use of corticosteroid injections provides mixed results in relief of pain and at times insufficient evidence to support their use. Injection of the tendon sheath with a depot corticosteroid (e.g., dexamethasone acetate, methylprednisolone acetate, hydrocortisone acetate) 0.5 to 1 ml mixed with an equal or double volume of 1% local anesthetic (e.g., lidocaine) has been utilized as a treatment, depending on severity and site. The injection is made blindly or proximal to the site of maximum tenderness if the specific inflammation site cannot be identified. Particular care should be taken not to inject the tendon per se (which offers greater resistance) because it may be weakened and rupture in active persons. Reexamination of a less inflamed site 3 or 4 days later often discloses the specific lesion, and a second injection can be made with greater precision. Rest of the injected part is advisable to diminish risk of tendon rupture. Although complications associated with intraarticular and soft tissue steroid injection are relatively uncommon, when a complication does occur, it can result in severe and disabling consequences for the subject. A small proportion of subjects fail to respond to only one injection of corticosteroid and some subjects who initially improve at four weeks had worst symptoms by six months. Therefore with this lack of consensus, no good evidence to support the use of local corticosteroid injections and the unknown long-term side-effects of using steroids, an alternative treatment must be sought.

In one embodiment of the present invention, pain associated with tendonitis of the knee, shoulders, hip, pelvis, spine, elbows, leg and foot may be treated with the compounds by injecting the compound in similar fashion as a localized corticosteroid injection. For example, in embodiments where the compound is used for the treatment/attenuation of pain associated with tendonitis or bursitis of the shoulder, a dose of the compound can be administered by injection into the subacromial bursa with the needle inserted into the space between the acromium and the humerus on the lateral aspect of the shoulder.

Osteoarthritis

The compounds of the present invention may be used to treat/attenuate pain associated with osteoarthritis (degenerative joint disease). Osteoarthritis is characterized by the breakdown of the joint's cartilage. Cartilage is the part of the joint that cushions the ends of bones. Cartilage breakdown causes bones to rub against each other, causing pain and loss of movement. Most commonly affecting middle-aged and older people, osteoarthritis can range from very mild to very severe. It affects hands and weight-bearing joints such as knees, hips, feet and the back. There are many factors that can cause osteoarthritis, including but not limited to age, genetics, obesity, sports-related activities, work-related activities, or accidents. Treatment of osteoarthritis focuses on decreasing pain and improving joint movement, and may include: Exercises to keep joints flexible and improve muscle strength; many different medications are used to control pain, including corticosteroids and NSAIDs, glucocorticoids injected into joints that are inflamed and not responsive to NSAIDS. For mild pain without inflammation, acetaminophen may be used; heat/cold therapy for temporary pain relief, joint protection to prevent strain or stress on painful joints; surgery (sometimes) to relieve chronic pain in damaged joints; and weight control to prevent extra stress on weight-bearing joints.

Pain associated with osteoarthritis may be treated/attenuated with the compounds administered, e.g., by intra-articular injection at the affected site, including but not limited to orthopedic disorders of the knee such as osteoarthritis, shin splints, medial tibial stress syndrome, bursitis, tendonitis (patellar tendonitis); tears of the anterior cruciate ligament (blown out knee), posterior cruciate ligament, medial collateral ligament and lateral collateral ligament; arthritis of the knee; meniscal cartilage tear; Runner's conditions such as iliotibial band syndrome and Pes Anserine bursitis; torn meniscus and limited cartilage defects of the knee; orthopedic disorders of the shoulders including, but not limited to, bursitis, dislocation, separation, impingement and tear of the rotator cuff, tendonitis, adhesive capsulitis (frozen shoulder) and fractures.

Rheumatoid Arthritis

The compounds may be used to treat/attenuate pain associated with rheumatoid arthritis. Rheumatoid arthritis is a chronic, systemic, inflammatory disease that chiefly affects the synovial membranes of multiple joints in the body. Because the disease is systemic, there are many extra-articular features of the disease as well. Rheumatoid Arthritis can affect many joints in the body, including the knee, ankle, elbow, and wrist. Joints that are actively involved with the disease are usually tender, swollen, and likely demonstrate reduced motion. The disease is considered an autoimmune disease that is acquired and in which genetic factors appear to play a role. The compounds may be administered via intra-articular injection in a location and fashion similar to that currently utilized with respect to localized injections of corticosteroids.

There are several different classes of drugs utilized to treat patients with the various types of rheumatic disease which maybe used in addition to treatment with the compounds of the present invention, including analgesics to control pain, corticosteroids, uric acid-lowering drugs, immunosuppressive drugs, nonsteroidal anti-inflammatory drugs, and disease-modifying antirheumatic drugs.

Back Pain

The compounds may be used to treat/attenuate pain associated with back pain. Back pain is the second most common reason for doctor visits in the U.S. The causes of lower back pain are numerous. Some of the more common causes of lower back pain are: sudden injury to the back such as may occur in an auto accident, fall, sports, or other manner; gynecological conditions such as endometriosis, menstrual cramps, fibroid tumors, and pregnancy are sometimes the cause of lower back pain in women; and stress to the muscles, nerves, or ligaments in the lower back. Slipped discs, pinched nerves, sciatica, aging, and infections are other common causes of lower back pain. The treatment of lumbar strain consists of resting the back (to avoid re-injury), medications to relieve pain and muscle spasm, local heat applications, massage, and eventual (after the acute episode resolves) reconditioning exercises to strengthen the low back and abdominal muscles Zygapophysial joints, better known as facet or "Z" joints, are located on the back (posterior) of the spine on each side of the vertebrae where it overlaps the neighboring vertebrae. The facet joints provide stability and give the spine the ability to bend and twist. They are made up of the two surfaces of the adjacent vertebrae, which are separated by a thin layer of cartilage. The joint is surrounded by a sac-like capsule and is filled with synovial fluid (a lubricating liquid that reduces the friction between the two bone surfaces when the spine moves and also nourishes the cartilage). A problem (such as inflammation, irritation, swelling or arthritis) in the facet joint may cause low back pain. Diagnostic tests can show an abnormality in a facet joint, which may suggest that the facet joint is the source of the pain. However, sometimes normal study results can be present while the facet joint is still the source of pain, and abnormal results do not always implicate the facet joint.

To determine if a facet joint is truly the source of back pain, an injection of local anesthetic (.e.g, as a block) may be utilized. If an injection of a small amount of anesthetic or numbing medication into the facet joint reduces or removes the pain, it indicates that the facet joint may be the source of the pain. This is diagnostic use of the facet joint injection. Once a facet joint is pinpointed as a source of pain, therapeutic injections of anesthetic agents and anti-inflammatory medications may give pain relief for longer periods of time. The compounds may be administered in such situations to attenuate such pain.

Facet joint injections are performed while the patient is awake, under a local anesthetic, and able to communicate. Sometimes, the health care provider may also administer drugs to make the patient more comfortable during the procedure. The injection is usually performed while the patient is lying on his or her stomach on an X-ray table. EKG, blood pressure cuffs and blood-oxygen monitoring devices may be hooked up prior to the injection process. Once the proper site has been determined, the physician will inject the anesthetic (often lidocaine or bupivicaine) and the anti-inflammatory (usually a corticosteroid.). This process may then be repeated depending on the number of affected facet joints.

The compounds may be administered via injection to treat back pain, e.g., in a location and fashion similar to that currently utilized with respect to localized injections of corticosteroids.

Heel Spur

The compounds of the present invention may be used to treat/attenuate pain associated with a heel spur, which is a projection or growth of bone where certain muscles and soft tissue structures of the foot attach to the bottom of the heel. Most commonly, the plantar fascia, a broad, ligament-like structure extending from the heel bone to the base of the toes becomes inflamed, and symptoms of heel pain begin. As this inflammation continues over a period of time, with or without treatment, a heel spur is likely to form. If heel pain is treated early, conservative therapy is often successful arid surgery is usually avoided. Early signs of heel pain are usually due to plantar fasciitis, the inflammation of the plantar fascia. It is probably the most common cause of heel pain seen by the podiatrist. It is seen in all groups of people; runners, athletes, week-end warriors, people who have jobs requiring a fair amount of standing, walking, or lifting, and those who have recently gained weight. Initially, patients receive taping of the foot and when indicated, cortisone injections or a short course an anti-inflammatory medication, taken orally. Exercises, night splints, and physical therapy are used as adjunct methods to try to reduce the inflammation. If successful, a custom made in shoe orthotic is made to control the abnormal stress and strain on the plantar fascia resulting in remission of the majority of the symptoms.

When the compound is used for the treatment of plantar fascia, the dose of the compound is preferably administered by injection into the affected area. When surgery is required, the compound is preferably administered by infiltration into the heel bone.

Laparoscopic Cholecystectomy

The compounds may be used to treat/attenuate pain associated with laparoscopic cholecystectomy. Laparoscopic cholecystectomies have virtually replaced open surgical cholecystectomy. However, patients undergoing laparoscopic cholecystectomies still have pain. Pain control following surgery typically includes use of opioids, especially within the first several days after surgery. The administration of the compounds in a patient who has undergone a laparoscopic cholecystectomy may reduce the amount of opioid consumption and postoperative pain scores associated with the procedure. In patients suffering from pain associated with a laparoscopic cholecystectomy, the dose of the compound may be administered either by injection, infiltration or both injection and infiltration. When the dose of compound is administered by injection, the compound may be injected directly the site of incision or to the immediate area surrounding the surgical site.

The compounds may be used to treat/attenuate pain associated with other laparoscopic surgical procedures, as well.

In further embodiments, the compounds of the present invention may be useful for improving sleep. The improved sleep may be a direct result of the effectiveness of the compounds to reduce and/or alleviate pain, e.g., neuropathic pain thus allowing a patient to experienced improved sleep.

The compounds may be administered as a single dose in a therapeutically effective amount to a discrete site in a patient in need thereof. In other embodiments, the compounds may be administered in multiple doses to obtain the desired pharmacological effect. The quantity of compound to be administered will be determined on an individual basis, and will be based on the pharmacological potency of the drug, the route of administration and at least in part on consideration of the individual's size, the severity of the symptoms to be treated and the results sought. In general, quantities of the compound sufficient to eliminate the unwanted condition will be administered. The actual dosage (concentration and volume) and the number of administrations per day will depend on the pharmacokinetic properties to be achieved (anesthesia or analgesia) and the mode of drug administrations, for example, by topical doses to the eye or the mucous membranes of the mouth, or by dermal application to the skin or by injections to achieve infiltration anesthesia or nerve blocks.

Administration of the compounds according to the methods of the present invention provides for a long duration of anesthesia/analgesia. In comparison, the duration of action of these compounds is longer when compared to lidocaine, the R-isomer and the racemic mixture when administered at the same concentration. In certain embodiments, administration of the compounds according to the methods of the present invention provides anesthesia/analgesia for at least about 5 minutes to about 48 hours. In other embodiments, administration of the compounds may provide anesthesia and/or analgesia for about 15 minutes to about 24 hours. In certain embodiments a depot formulation may provide anesthesia and/or analgesia for about 24 hours to about 26 weeks, e.g., parenteral administration.

Since the S-isomer offers a long duration of local anesthesia/analgesia, even without the use of vasoconstrictors, and since the compounds have inherent analgesic activity, these compounds may be suited for combination with other active agents. For example, injectable solutions may contain a vasoconstrictor (e.g. epinephrine or vasopressin); a solution for infusion or regional anesthesia may contain glucose or dextrose, a jelly for urogenital topical procedures may contain thickening agents (e.g. hydroxypropylmethylcellulose); a preparation for topical or dermal application may contain penetration promoting agents (e.g. hydroxypolyethoxydodecane, DMSO, DMAC); sprays for topical anesthesia of the mouth and oropharynx may contain saccharin and alcohol, ointments for accessible mucous membranes may contain a lubricant. The compound of the invention can also be administered together with other membrane stabilizers (local anesthetics), for example to form eutectic mixtures.

In certain embodiments, the compounds may be suitable for co-administration with other analgesic drugs such as, but not limited to, opioid analgesics, steroidal or non-steroidal anti-inflammatory agents and salicylates. In other embodiments, the compounds may be co-administered with capsaicinoids such as capsaicin. In combination with capsaicin, the compounds may offer improved analgesic activity without the initial pain associated with capsaicinoid administration.

In certain embodiments, co-administration of capsaicin with a compound of the present invention, e.g., S-LAC-34, may a provide for a potentiation of the local anesthetic activity of the compound. In other embodiments, co-administration of these two agents may provide an improvement of the therapeutic response in a patient suffering from neuropathic pain.

In certain embodiments, the concentration of capsaicinoid may range from about 0.0001% to about 10% percent. In other embodiments, the concentration of capsaicinoid may range from about 0.01% to 1%. In other embodiments, the capsaicinoid may range from about 0.1% to 1%.

The co-administration of a compound of the present invention with additional analgesic agents may be valuable in patients suffering from chronic pain.

In other embodiments of the present invention, the compounds may be co-administered with vasoconstrictor agents, the spreading agent hyaluronidase and/or hyaluronic acid.

When a dose of the compound is administered parenterally via injection or implantation, the injection or implantation volume of will depend on the localized site of administration. Suitable injection and implantation volumes to be delivered range from about 0.1 to about 20 ml. In certain embodiments, the injection or implantation volume may be from about 0.5 to about 10 ml and in other embodiments from about 1.0 to about 5 ml, depending on the site to be treated.

Volumes for administration via infiltration may range from 0.1 to 1000 ml. In other embodiments, infiltration volumes range from 1 ml to about 100 ml and from about 5 ml to about 30 ml.

Preparation of the S-Isomers

There are several strategies to prepare enantiomers of drugs. These include: i) resolution of the racemate drug, for example by fractional crystallization of diastereomeric derivatives; ii) separation of the racemate by chiral chromatography; iii) synthesis of the desired enantiomer by using a chiral starting material; and iv) generation of the chiral center by synthesis with a chiral auxiliary molecule. All four strategies may be used to prepare S-LAC-34. Three of the strategies (i-iii) are further described herein.

Depending on the process conditions and the starting materials, the end product may be obtained either as the free base, polymorh(s), metabolite, derivatives or as an acid addition salt thereof. In certain embodiments, the basic, neutral or mixed salts may be obtained, as well as hemi-, mono-, sesqui-, or polyhydrates. The acid addition salts of the compounds described herein may be transformed in a manner known per se into the free base using basic agents such as an alkali or by ion exchange. In certain embodiments, the free bases obtained may form salts with organic or inorganic acids.

The preparation of acid addition salts may be performed using acids which form suitable therapeutically acceptable salts. Such acids include, but are not limited to hydrohalogen acids, sulfuric, phosphoric, nitric, and perchloric acids; aliphatic, alicyclic, aromatic, heterocyclic carboxy or sulfonic acids, such as acetic, formic, propionic, succinic, glycolic, lactic, malic, tartaric, citric, ascorbic, maleic, hydroxymaleic, pyruvic, phenylacetic, benzoic, p-aminobenzoic, anthranilic, p-hydroxybenzoic, salicylic or p-aminosalicylic acid, embonic, methanesulfonic, ethane sulfonic, hydroxyethanesulphonc, ethylenesulphonic, halogenbenzenesulphonic, toluenesulfonic, naphtylsulfonic, or sulfanilic acids; methionine, tryptophane, lysine or arginine.

In certain embodiments of the present invention, the compounds of the present invention may be prepared by reaction between two agents, one of which is an S-enantiomer. For example, the compounds may be prepared according to the following methods:

a) by reacting a compound of formula 2

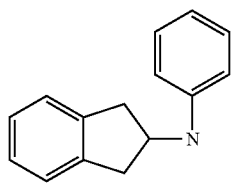

with an S-enantiomer of a compound of formula 3,

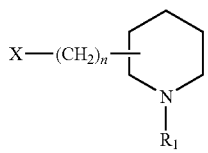

wherein $R_1$ represents a lower alkyl or hydroxyalkyl containing 1 to 4 carbon atoms or a substituted or unsubstituted phenyl and X is a halogen (bromo, chloro, fluoro, iodo) or a reactive esterified hydroxyl group, to form a compound of formula 1; and b) hydrogenating a compound of formula 1, wherein $R_1$ is a residue removable by means of hydrogenolysis to give a compound of formula 1, wherein $R_1$ is hydrogen; and c) hydrolyzing a compound of formula 1, wherein $R_1$ is a residue removable by means of hydrolysis, to form a compound of formula 1, wherein $R_1$ is hydrogen; and d) transforming free bases obtained into their salts or transforming salts into their free bases.

In certain other embodiments of the present invention, S-LAC-34 may be prepared by: (a) sequential conversion of a N-protected L-pipecolic acid, i.e., the S-enantiomer, to a corresponding diazomethyl ketone. The corresponding ketone is then converted to a methyl ester and the methyl ester then converted to a primary alcohol. The primary alcohol is then converted to an S-alkyl halide; (b) reacting the resulting S-alkyl halide with 2-(phenylamino)indane; and (c) removing the N-protecting group to obtain S-LAC-34.

In certain other embodiments, the S-LAC-34 of the present invention may be prepared by: (a) sequential conversion of a N-protected L-pipecolic acid to a corresponding diazomethyl ketone. The corresponding ketone is then converted to a methyl ester and the methyl ester then converted to a primary alcohol. The primary alcohol is then converted to an S-alkyl halide; (b) removing the N-protecting group; (c) introducing a different (second) protecting group; (d) reacting the resulting S-alkyl halide with 2-(phenylamino)indane, and (e) removing the N-protecting group to obtain S-LAC-34.

In yet another embodiment, the S-LAC-34 of the present invention may be prepared by: (a) sequential conversion of a N-protected L-pipecolic acid to a corresponding diazomethyl ketone. The corresponding ketone is then converted to a methyl ester and the methyl ester then converted to a primary alcohol. The primary alcohol is then converted to an S-alkyl halide; (b) removing the N-protecting group; and reacting the resulting S-alkyl halide, as a salt, with 2-(phenylamino)indane.

The N-protecting group may be benzyl or benzyloxycarbonyl. When the N-protecting group is benzyl, the benzyl may be removed by hydrogenolysis. When the N-protecting group is benzylkoxycarbonyl, the benzyloxycarbonyl may be removed by acid hydrolysis.

In certain embodiments, S-2-(2-haloethyl)piperidine salt is S-2-(chloroethyl)piperidine hydrochloride. The S-2-(chloroethyl)piperidine hydrochloride may be combined with 2-(phenylamino)indane in the presence or absence of, independently, a solvent and a catalyst. The mixture may be heated to a temperature of from about 120° C. to about 160° C. for a time period of from about 24 hours to about 72 hours. The 2-(phenylamino)indane and S-2-(2-chloroethyl)piperidine hydrochloride may be combined with 1,3-dimethylimidazolidinone in the presence of 2,6-lutidine. The resulting mixture may then be heated to a temperature of from about 120° C. to about 160° C. under an atmosphere of nitrogen for a period of from about 24 hours to about 72 hours with constant stirring. Solvent may then be added and the mixture heated. Once heated the hydrochloride salt of the mixture may be cooled and filtered to obtain the S-LAC-34.

In certain other embodiments, S-LAC-34 may be prepared by resolution of racemic LAC-34 by fractional crystallization of a diastereomeric salts with chiral acids. In certain embodiments, the chiral acid may be selected from the group consisting of tartaric acid, di-(p-toluyl)-tartaric acid, dibenzoyl-tartaric acid or mandelic acid.

In certain embodiments, S-LAC-34 may be prepared by separation of the enantiomers from racemic LAC-34 using chromatography on a chiral support. The chiral support may be HPLC or column chromatography.

The invention is more fully understood by the following examples.

DETAILED DESCRIPTION OF PREFERRED EMBODIMENTS

S-2-{2-[N-(2-indanyl)-N-phenylamino]ethyl}piperidine (S-LAC-34) has now been synthesized according to the following methodology. (Boc=benzyloxycarbonyl).

EXAMPLE I

The Synthesis Of (S)-Lac-34 Hydrochloride From Chiral Starting Material

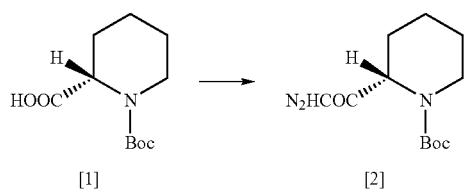

Isobutyl chloroformate (5.65 ml) was added dropwise to a solution of 9 g of Boc-L-pipecolic acid [1] and 4.97 ml of N-methylmorpholine in 150 ml of anhydrous tetrahydrofuran (THF) at −30° C., and the reaction mixture was kept at −30° C. for 1 hour. Then 250 ml of a solution of diazomethane (prepared from 43 g of diazogen) in diethyl ether was added, and the mixture was stirred at room temperature overnight. Acetic acid (5 ml) was added dropwise to destroy excess diazomethane, and the reaction mixture was evaporated to dryness. The residue was dissolved in diethyl ether, washed with water, brine, and dried over $Na_2SO_4$. After evaporation, 8.9 g of crude diazomethyl ketone [2] was obtained, and used directly in the next step.

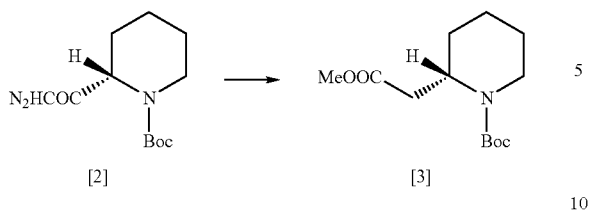

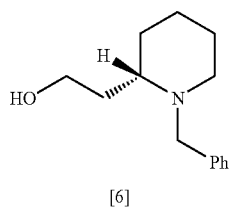

-continued

Compound [2] (8.9 g) was dissolved in 100 ml anhydrous methanol, and 1.0 g of silver benzoate was added with stirring at room temperature. After 3 hours, 50 ml of brine was added, and the mixture was filtered through Celite. The filtrate was evaporated to remove methanol, and the resulting aqueous solution was extracted with ethyl acetate three times, the combined organic extract washed with brine, and dried over $Na_2SO_4$. The dried organic layer was evaporated, and the residue was purified by column chromatography (silica gel) to give 7.64 g of N-Boc β-amino acid ester [3].

A mixture of compound [5], 2.3 ml of benzyl bromide, 5 g of potassium carbonate in 00 ml of acetonitrile was refluxed overnight. The solvent was removed in vacuo, and 2N hydrochloric acid was added until the pH was ~4. The mixture was extracted with diethyl ether to remove neutral impurities. The aqueous layer was neutralized with 2N sodium hydroxide to pH ~8, extracted with ethyl acetate three times, the combined organic extract washed with water, brine, and dried over $Na_2SO_4$. The organic layer was evaporated to dryness to give 2.5 g of N-benzyl protected alcohol [6].

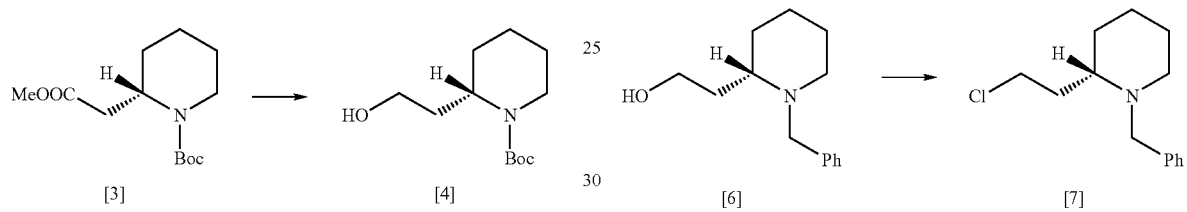

Lithium aluminum hydride (0.453 g) was added to a solution of 4.0 g of compound [3] in 100 ml of anhydrous diethyl ether at 0° C. The suspension was stirred at 0° C. for 1 hour, and then poured onto ice-water. The mixture was filtered, and the filtrate was extracted with diethyl ether three times. The combined organic extract was washed with brine and dried over $Na_2SO_4$. After evaporation, 3.48 g of crude alcohol [4] was obtained and used in the next step without purification.

A solution of compound [6] (2.5 g), 3 ml of thionyl chloride, two drops of concentrated hydrochloric acid in 50 ml of chloroform was heated at reflux overnight. The mixture was evaporated to dryness, and 50 ml of saturated aqueous sodium bicarbonate was added. The aqueous layer was extracted with ethyl acetate three times, and the combined organic extract was washed with water, brine, and dried over $Na_2SO_4$. After evaporation, the residue was purified by column chromatography (silica gel) to give 1.7 g of the corresponding alkyl chloride [7].

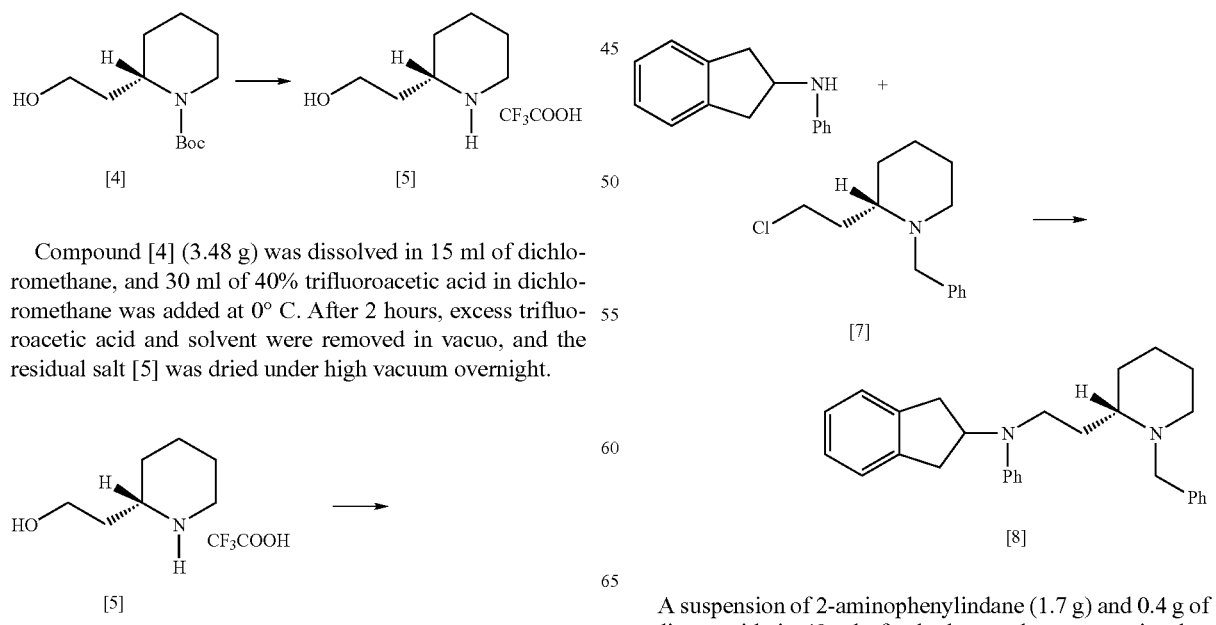

Compound [4] (3.48 g) was dissolved in 15 ml of dichloromethane, and 30 ml of 40% trifluoroacetic acid in dichloromethane was added at 0° C. After 2 hours, excess trifluoroacetic acid and solvent were removed in vacuo, and the residual salt [5] was dried under high vacuum overnight.

A suspension of 2-aminophenylindane (1.7 g) and 0.4 g of sodium amide in 40 ml of anhydrous toluene was stirred at room temperature for 3 hours. A solution of 1.7 g of compound [7] in 5 ml of anhydrous toluene was added. The reaction mixture was refluxed overnight and poured onto ice-water after cooling. The mixture was extracted with ethyl acetate three times, and the combined organic layer was washed and dried over $Na_2SO_4$. After evaporation, 1.1 g of pure N-benzyl (S)-LAC-34 [8] was obtained by column chromatography (silica gel).

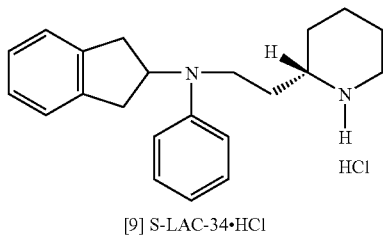

[9] S-LAC-34•HCl

A mixture of 1.1 g of compound [8] and 200 mg of 10% Pd—C in 50 ml of ethyl acetate was stirred under 30 psi of hydrogen gas at room temperature for 5 hours. The reaction mixture was filtered through Celite, and the filtrate was evaporated to dryness. The residue was dissolved in 10 ml of anhydrous diethyl ether, and 10 ml of 2N hydrogen chloride in diethyl ether was added. The 650 mg of desired (S)-LAC-34 hydrochloride [9] was obtained by filtration.

$^1$NMR ($CDCl_3$)

δ: 7.15~7.27 (m, 6H, H-Ph), 6.74~6.86 (m, 3H, H-Ph), 4.51~4.68(m, 1H, PhNCH), 2.42~3.40 (m, 10H, $C_6H_4$(CH$_2$)$_2$—, PhNCH$_2$—, —CHNCH$_2$—), 1.25~1.77 (m, 8H, —NCH$_2$CH$_2$CH$_2$—, —NCH$_2$CH$_2$—).

Biological Testing

EXAMPLE II

Topical Anesthetic Activity

Aliquots (0.25 ml) of test solutions are applied into the conjunctival sac of conscious rabbits (either sex; 2-4 kg) and the eye-lids are kept closed for approximately 20 sec. The corneal reflex is checked before application of the test solution and every 5 min thereafter. To test the corneal reflex, the cornea is touched six times with a stalked elastic bristle. The duration of anesthesia is calculated as the period from the time-point when the animal does not feel any of the six touches by the bristle to the time point when the animal again reacts to three of the six touches. To verify the reversibility of the topical anesthetic effect, the testing is continued until the animal reacts to all six touches of the bristle.

EXAMPLE III

Dermal Anesthetic Activity

Approximately 18-24 hours before each experiment, the skin on the back of male or female guinea pigs was shaved and depilated with a commercially available hair remover. The anesthetic action of each agent following dermal application was determined using a "pin-prick" method as described by Aberg (Acta Pharmacol Toxicol, 1972, 31: 273-286). Before and at various intervals after treatment, the area of the skin was tested for the presence or absence of a skin twitch in response to six standardized dermal probings with a pointed metal "algesimeter" at a predetermined maximum load of 10 grams. The average number of probings not producing a skin twitch response was designated as the "anesthetic score". In this test system no response to six stimuli represents a "maximal anesthetic activity". In the present calculations, the dermal anesthetic activity was calculated from the time of removal of the test article formulation from the skin until skin twitch responses to all but one pinprick were identified. In experiments on the dermal anesthetic activity, a single area of skin 1 inch square was marked off on the middle of the back of each animal. This area was covered by a 1 inch square, 16 layer thick gauze pad onto which was deposited 0.45 ml of a 10% solution of the test agent dissolved in a mixture of water and DMSO. The gauze pad was covered with a 1.5 inch square sheet of Saran Wrap™ which was attached to the surrounding skin with tape. The entire area was then covered by wrapping an elastic bandage around the trunk of the animal. After a predetermined duration of treatment, the coverings were removed and the skin assessed for the presence of anesthesia as described above. Dermal anesthesia tests were performed at ten-minute intervals to measure onset time and duration of dermal anesthetic activity; comparisons were made with reference compounds and vehicle. All test compounds were in the base form and dissolved in DMSO/water when tested for dermal anesthesia.

EXAMPLE IV

Local (Infiltration) Anesthetic Activity

Approximately 18-24 hours before each experiment, the skin on the back of male guinea pigs is shaved and depilated with a commercially available hair remover. The anesthetic action of each agent following intradermal injection is determined using a "pin-prick" method as described by Aberg (Acta Pharmacol Toxicol, 1972, 31: 273-286). Before and at various intervals after treatment, the area of the skin is tested for the presence or absence of skin twitch in responses to six standardized cutaneous probings with a pointed metal "algesimeter" at a predetermined maximum force of 20 grams. The average number of probings not producing a skin twitch response is designated as the "anesthetic score". In this test system six responses to six stimuli represents "no anesthetic activity" and no response to six stimuli represents a "maximal anesthetic activity". In experiments with intradermal injections, the backs of the guinea pigs are divided into four sections using a marking pen, and injections of 0.1 ml of 0.25%, 0.5% and 1.0% solutions of the test compounds as salts in physiological saline, vehicle (physiological saline) and at least one reference compound are made, one injection into each of the four defined areas.

EXAMPLE V

Analgesic Activity: Effects on Mononeuropathic Pain Thresholds

Peripheral mononeuropathy is induced in rats by loose ligation of the sciatic nerve in anesthetized rats. Fourteen days later, the nociceptive threshold is evaluated after animal dosing with drug or vehicle, using graded paw pressure testing to assess hyperalgesia.

EXAMPLE VI

Analgesic Activity: Effects on Diabetic Neuropathic Pain Thresholds

Diabetes is induced in rats by intraperitoneal injection of streptozotocin. Three weeks later, the nociceptive threshold is measured after animal dosing using the paw pressure to assess hyperalgesia.

EXAMPLE VII

Acute Intravenous Toxicity in Mice

Mice (males) of the NMRI strain, weighing 20 grams to 22 grams are used after a stabilization period of at least ten days at the testing facility and at least one hour in the laboratory. Food but not water is withheld from all animals for 16 hours before the test. The animals are again given free access to food starting two hours after the drug administration that usually takes place around 9.00 AM. All animals are observed daily for 7 days post dosing.

Those skilled in the art will recognize, or be able to ascertain, using no more than routine experimentation, many equivalents to the specific embodiments of the invention described herein. The compound of the present invention may be used also for other indications, such as for example to prevent or treat smooth muscle spasms, cardiac arrhythmias, convulsions and hiccup. Formulations of the compound of the invention may also include liposomal formulation, particularly in formulations used for dermal anesthesia and dermal analgesia. Eutectic formulations can be obtained by mixing the compound of the formulation with other therapeutic or chemical entities. All equivalents are intended to be encompassed in the scope of the present invention.

What is claimed is:

1. A method of relieving neuropathic pain in a patient in need thereof, comprising administering to a discrete site in a patient in need thereof a neuropathic pain-relieving effective amount of the compound S-2-{2-[N-(2-indanyl)-N-phenylamino]ethyl}piperidine:

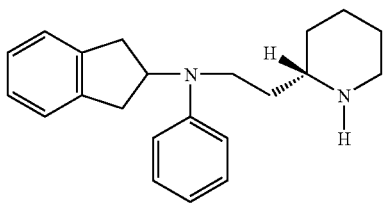

wherein administration of the compound to the discrete site provides a duration of action that is longer than that of the corresponding racemate and the corresponding R-isomer.

2. The method of claim 1, wherein said pain is selected from the group consisting of neuropathic pain caused by AIDS/HIV, Herpes Zoster, syphilis, diabetes, and autoimmune diseases.

3. The method of claim 1, wherein said site is an area with neuropathic pain.

4. The method of claim 1, wherein administration of the compound provides relief of pain for about 5 minutes to about 48 hours.

5. The method of claim 1, wherein administration of the compound provides relief of pain for about 24 hours to about 26 weeks.

6. The method of claim 1, wherein the compound is a more than 95% optically pure S-isomer.

7. The method of claim 1, wherein the compound is a more than 97% optically pure S-isomer.

8. The method of claim 1, wherein the compound is a more than 99% optically pure S-isomer.

9. The method of claim 1, wherein the compound attenuates or relieves neuropathic pain selected from the group consisting of pain from nerve injury, pain from neuralgia, pain from myalgias, pain associated with painful trigger points, pain from tumors in soft tissues, pain associated with neurotransmitter-dysregulation syndromes and neuropathic pain associated with orthopedic disorders selected from the group consisting of neuropathic conditions of the foot, knee, hip, spine, shoulders, elbow, hand, head and neck.

10. The method of claim 1, wherein said site is a surgical site.

11. The method of claim 1, wherein said neuropathic pain is associated with a condition selected from the group consisting of tendonitis, bursitis, osteoarthritis, and rheumatoid arthritis.

12. The method of claim 1, wherein said neuropathic pain is associated with an orthopedic disorder of the foot selected from the group consisting of heel spurs, corns, bunions, Morton's neuroma, hammertoes, ankle sprain, fractures of the ankle or metatarsals or sesamoid bone or toes, plantar fascitis and injuries to the achilles tendon.

13. The method of claim 1, wherein said neuropathic pain is associated with an orthopedic disorder of the hand selected from the group consisting of arthritis, carpal tunnel syndrome, and ganglion cysts.

14. The method of claim 1, wherein said neuropathic pain is associated with a disorder selected from the group consisting of lateral epicondylitis, medial epicondylitis, rotator cuff tendonitis, DeQuervian's tenosynovitis, and trigger finger/trigger thumb.

15. The method of claim 1, wherein said neuropathic pain is associated with a disorder selected from the group consisting of Paget's disease, scoliosis, contusions, sprains, strains, lower back pain, and heel spur.

16. The method of claim 1, wherein said neuropathic pain is associated with a bone fracture.

* * * * *